(12) United States Patent
Hall et al.

(10) Patent No.: US 8,153,850 B2
(45) Date of Patent: Apr. 10, 2012

(54) INTEGRATED BIOFUEL PRODUCTION SYSTEM

(75) Inventors: Kenneth R. Hall, College Station, TX (US); Mark T. Holtzapple, College Station, TX (US); Sergio C. Capareda, College Station, TX (US)

(73) Assignee: The Texas A&M University System, College Station, TX (US)

( * ) Notice: Subject to any disclaimer, the term of this patent is extended or adjusted under 35 U.S.C. 154(b) by 655 days.

(21) Appl. No.: 12/267,704

(22) Filed: Nov. 10, 2008

(65) Prior Publication Data

US 2009/0239279 A1    Sep. 24, 2009

Related U.S. Application Data

(63) Continuation-in-part of application No. 12/118,484, filed on May 9, 2008, now abandoned.

(60) Provisional application No. 60/917,467, filed on May 11, 2007.

(51) Int. Cl.
*C12P 5/02* (2006.01)

(52) U.S. Cl. ........ 585/240; 585/241; 585/242; 210/301; 210/603; 210/605; 48/197 A; 48/197 FM; 435/132; 435/135; 435/136; 435/140; 435/141; 435/148

(58) Field of Classification Search .......... 585/240–242, 585/408; 435/132, 135–136, 140–141, 148; 210/601, 603, 605
See application file for complete search history.

(56) References Cited

U.S. PATENT DOCUMENTS

| | | | |
|---|---|---|---|
| 3,936,353 A | 2/1976 | Chen |
| 4,439,272 A | 3/1984 | Nguyen |
| 4,848,249 A | 7/1989 | LePori et al. |
| 5,693,296 A | 12/1997 | Holtzapple et al. |
| 5,865,898 A | 2/1999 | Holtzapple et al. |
| 5,962,307 A | 10/1999 | Holtzapple et al. |
| 5,969,189 A | 10/1999 | Holtzapple et al. |
| 5,986,133 A | 11/1999 | Holtzapple et al. |
| 6,043,392 A | 3/2000 | Holtzapple |
| 6,130,260 A | 10/2000 | Hall et al. |
| 6,262,313 B1 | 7/2001 | Holtzapple et al. |
| 6,323,247 B1 | 11/2001 | Hall et al. |

(Continued)

FOREIGN PATENT DOCUMENTS

EP    0 366 138    5/1990

(Continued)

OTHER PUBLICATIONS

Pandey, M.P. et al. (2011). Chemical Engineering & Technology, 34(1), 29-41.*

(Continued)

*Primary Examiner* — Walter D Griffin
*Assistant Examiner* — Brian McCaig
(74) *Attorney, Agent, or Firm* — Baker Botts L.L.P.

(57) ABSTRACT

According to an embodiment, a biomass conversion subsystem produces methane and/or alcohol and residual biomass. A pyrolysis or a gasification subsystem is used to produce thermal energy and/or process gasses. The thermal energy may be stored thermal energy in the form of a pyrolysis oil. A fuel conversion subsystem produces liquid hydrocarbon fuels from the methane and/or alcohol using thermal energy and/or process gasses produced by the gasification or pyrolysis subsystem. Because the biomass production system integrates the residual products from biomass conversion and the residual thermal energy from pyrolysis or gasification, the overall efficiency of the integrated biomass production system is greatly enhanced.

55 Claims, 19 Drawing Sheets

U.S. PATENT DOCUMENTS

| | | | |
|---|---|---|---|
| 6,478,965 | B1 | 11/2002 | Holtzapple et al. |
| 6,602,920 | B2 | 8/2003 | Hall et al. |
| 7,119,240 | B2 | 10/2006 | Hall et al. |
| 2005/0065391 | A1* | 3/2005 | Gattis et al. ............... 585/943 |
| 2005/0112739 | A1* | 5/2005 | Golubkov ............... 435/161 |
| 2008/0176301 | A1 | 7/2008 | Granda et al. |
| 2008/0280338 | A1 | 11/2008 | Hall et al. |

FOREIGN PATENT DOCUMENTS

| | | |
|---|---|---|
| EP | 1 227 074 | 7/2002 |
| EP | 1 908 815 | 4/2008 |
| WO | WO 2008/109129 | 9/2008 |

OTHER PUBLICATIONS

Notification of Transmittal of the International Search Report and the Written Opinion of the International Searching Authority, or the Declaration (EPO) for PCT/US2008/063274; 13 pages, Apr. 12, 2008.

Holtzapple et al. "Biomass Conversion to Mixed Alcohol Fuels Using the MixAlco Process," Applied Biochemistry and Biotechnology, vol. 77-79;pp. 609-631; 1999.

Notification of Transmittal of the International Search Report and the Written Opinion of the International Searching Authority, or the Declaration (EPO) for PCT/US2009/061215; 14 pages, Nov. 19, 2010.

Boateng, et al.; "Pyrolysis of hull-enriched byproducts from the scarification of hulled barley," Journal of Analytical and Applied Pyrolysis; www.sciencedirect.com; pp. 95-103, 2006.

Granda, et al.; "Carboxylate Platform: The MixAlco Process part 2: Process Economics," Applied Biochemistry and Biotechnology, vol. 156; pp. 537-554, Oct. 10, 2007.

Holtzapple et al. MixAlco Process: Fuels and Chemicals from Biomass (online); retrieved from www.simhq.org/meetings/30symp/30sympProgramFront;pp. 3 and 42; May 2008.

\* cited by examiner

| FEEDSTOCK SUITABILITY BY BIO-CONVERSION PROCESS | | | | | | |
|---|---|---|---|---|---|---|
| Feedstock Source | Carboxolate Salts Process | Gas to Liquids | Anaerobic Digestion for Biogas | Anaerobic Digestion for Acetic Acid | Pyrolysis for Producer Gas | Enzymes for Sugars to Acid |
| Fresh animal manures (dairy and beef cattle, swine, poultry) | 3 | 3 | 3 | 3 | 2 | 1 |
| Kitchen food wastes | 3 | 3 | 3 | 3 | 2 | 3 |
| Food processing plant wastes | 3 | 3 | 3 | 3 | 2 | 3 |
| Beverage waste, syrups, molasses | 3 | 3 | 3 | 3 | 2 | 3 |
| Thin and whole stillage, wet distillers grain | 3 | 3 | 3 | 3 | 2 | 3 |
| Raw human sewage | 3 | 3 | 3 | 3 | 1 | 1 |
| Treated sewage sludge, biosolids | 3 | 3 | 3 | 3 | 2 | 1 |
| Fats, oils and greases | 3 | 3 | 3 | 3 | 2 | 1 |
| Meat packing wastes, paunche | 3 | 3 | 3 | 3 | 2 | 2 |
| Processed MSW lignocellulosic wastes | 2 | 3 | 1 | 1 | 3 | 2 |
| Processed MSW plastics and tire wastes | 0 | 3 | 0 | 0 | 0 | 0 |
| Pulp and paper sludges | 3 | 3 | 2 | 2 | 3 | 2 |
| Wood wastes (saw dust, chips, trimmings, beetle kill, etc.) | 1 | 3 | 1 | 1 | 3 | 3 |
| Landfill or digester gas | 0 | 3 | 0 | 0 | 0 | 0 |
| Energy crops (cane, sorghum, miscanthus, switch grass, etc.) | 3 | 3 | 1 | 2 | 3 | 3 |
| Energy crops (wood-poplar, aspen, willow, alder, etc.) | 2 | 3 | 1 | 2 | 3 | 3 |
| Crop residues (corn stover/cobbs, wheat or rice straw; etc.) | 2 | 3 | 1 | 1 | 3 | 3 |
| Algae (cyanobacteria), diatoms (bacillariophyceae), seaweed (sargassum) | 3 | 3 | 3 | 3 | 0 | 1 |

*FIG. 4*

Index for Suitability of Feedstock by Conversion Process
0 - None
1 - Low
2 - Moderate
3 - High

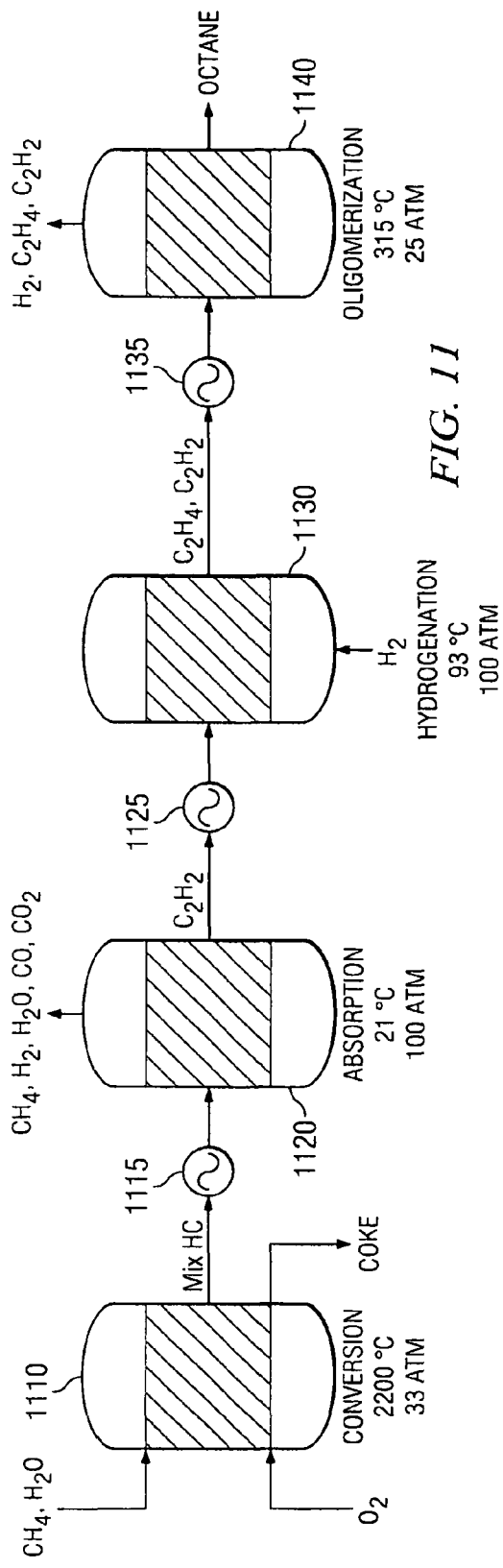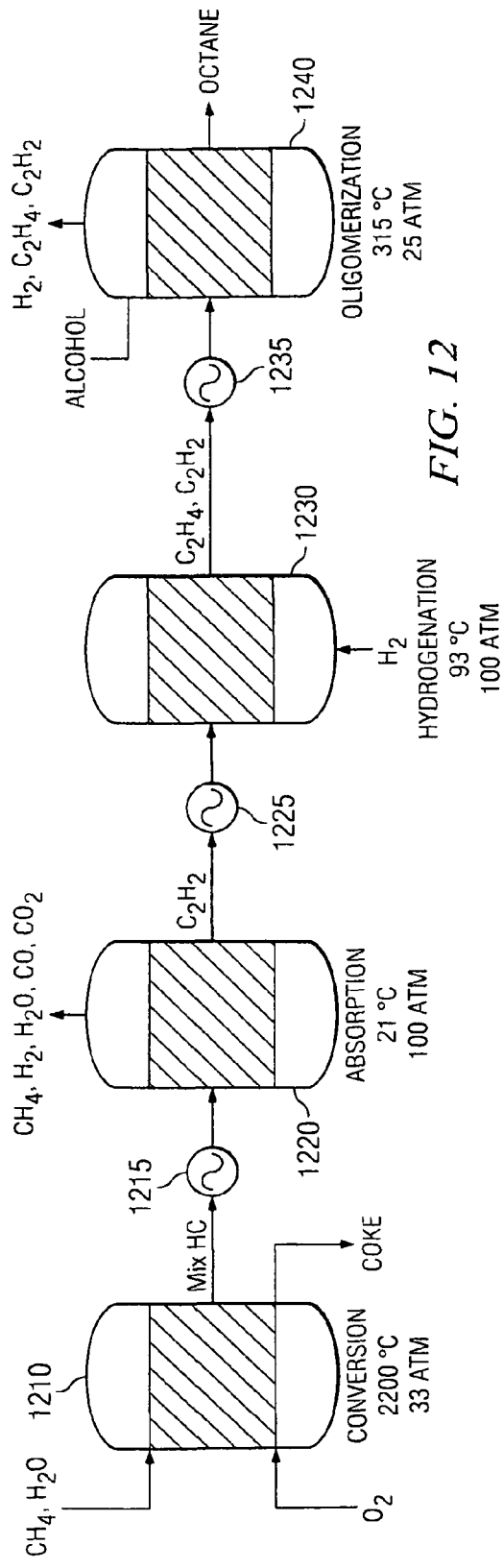

Mass and Energy Inputs and Outputs for Subsystem of Biomass Conversion System of FIG. 16

| | Biomass to Biogas | | | | Pyrolysis | | | | Biomass to Fuel | | | |
|---|---|---|---|---|---|---|---|---|---|---|---|---|
| | In | | Out | | In | | Out | | In | | Out | |
| Mass | MSW | 62.7 t/h | CH$_4$ | 23 t/h | RB | 76.3 t/h | H$_2$O | 72.8 t/h | CH$_4$ | 23 t/h | H$_2$O | 26.46 t/h |
| | H$_2$O | 340 t/h | H$_2$O | 340 t/h | H$_2$O | 72.8 t/h | Char | 19.9 t/h | H$_2$O | 5.75 t/h | N$_2$ | 1.89 t/h |
| | Inoculum | 125 t/h | RB | 76.3 t/h | Ca(OH)$_2$ | 52 t/h | Bio-oil | 100.4 t/h | O$_2$ | 41.16 t/h | H$_2$ | 1.97 t/h |
| | | | CO$_2$ | 88.4 t/h | Inoculum | 10.4 t/h | Gas | 18.4 t/h | N$_2$ | 1.89 t/h | C$_2$H$_2$ | 1.64 t/h |
| | | | | | | | | | H$_2$ | 0.59 t/h | C$_2$H$_4$ | 1.14 t/h |
| | | | | | | | | | | | CO | 12.71 t/h |
| | | | | | | | | | | | CO$_2$ | 13.32 t/h |
| | | | | | | | | | | | Coke | 0.14 t/h |
| | | | | | | | | | | | Biofuel | 6.58 t/h |
| Total Mass | 527.7 t/h | | 527.7 t/h | | 211.6 t/h | | 211.6 t/h | | 72.39 t/h | | 72.39 t/h | |
| Energy | 0 GJ/h | | | | 0 GJ/h | | 638.6 GJ/h | | 0 GJ/h | | 184 GJ/h | |

*FIG. 17*

Mass and Energy Inputs and Outputs for Subsystem of Biomass Conversion System of FIG. 18

| | Biomass to Alcohol | | | | Alcohol to Fuel | | | | Pyrolysis | | | |
|---|---|---|---|---|---|---|---|---|---|---|---|---|
| | In | | Out | | In | | Out | | In | | Out | |
| Mass | 100 t/h | MSW | 22 t/h | RB | 27.93 t/h | Alcohol | 17.02 t/h | Biofuel | 22 t/h | RB | 21 t/h | $H_2O$ |
| | 15 t/h | $Ca(OH)_2$ | 15 t/h | $Ca(OH)_2$ | 9.43 t/h | $H_2O$ | 20.34 t/h | $H_2O$ | 21 t/h | $H_2O$ | 5.74 t/h | Char |
| | 984 t/h | $H_2O$ | 992 t/h | $H_2O$ | | | | | 15 t/h | $Ca(OH)_2$ | 28.96 t/h | Bio-oil |
| | 27 t/h | Air | 27 t/h | Air | | | | | 3 t/h | Inoculum | 5.3 t/h | Gas |
| | 3 t/h | Inoculum | 3 t/h | Inoculum | | | | | | | | |
| | 42 t/h | $CaCO_3$ | 40 t/h | $CaCO_3$ | | | | | | | | |
| | 0.93 t/h | $H_2$ | 8 t/h | Scum | | | | | | | | |
| | | | 37 t/h | $CO_2$ | | | | | | | | |
| | | | 27.93 t/h | Alcohol | | | | | | | | |
| Total Mass | 1171.93 t/h | | 1171.93 t/h | | 37.36 t/h | | 37.36 t/h | | 61 t/h | | 61 t/h | |
| Energy | 0 GJ/h | | 0 GJ/h | | 0 GJ/h | | 0 GJ/h | | 0 GJ/h | | 251.3 GJ/h | |

*FIG. 19*

Mass and Energy Inputs and Outputs for Subsystem of Biomass Conversion System of FIG. 19

| | Biomass to Alcohol | | | | Alcohol to Fuel | | | | Pyrolysis | | | |
|---|---|---|---|---|---|---|---|---|---|---|---|---|
| | In | | Out | | In | | Out | | In | | Out | |
| Mass | 100 t/h | MSW | 22 t/h | RB | 27.93 t/h | Alcohol | 17.02 t/h | Biofuel | 22 t/h | RB | 21 t/h | $H_2O$ |
| | 15 t/h | $Ca(OH)_2$ | 15 t/h | $Ca(OH)_2$ | | | 10.91 t/h | $H_2O$ | 21 t/h | $H_2O$ | 5.74 t/h | Char |
| | 984 t/h | $H_2O$ | 992 t/h | $H_2O$ | | | | | 15 t/h | $Ca(OH)_2$ | 28.96 t/h | Bio-oil |
| | 27 t/h | Air | 27 t/h | Air | | | | | 3 t/h | Inoculum | 5.3 t/h | Gas |
| | 3 t/h | Inoculum | 3 t/h | Inoculum | | | | | | | | |
| | 42 t/h | $CaCO_3$ | 40 t/h | $CaCO_3$ | | | | | | | | |
| | 0.93 t/h | $H_2$ | 8 t/h | Scum | | | | | | | | |
| | | | 37 t/h | $CO_2$ | | | | | | | | |
| | | | 27.93 t/h | Alcohol | | | | | | | | |
| Total Mass | 1171.93 t/h | | 1171.93 t/h | | 27.93 t/h | | 27.93 t/h | | 61 t/h | | 61 t/h | |
| Energy | 0 GJ/h | | 0 GJ/h | | 0 GJ/h | | 0 GJ/h | | 0 GJ/h | | 0 GJ/h | |

FIG. 21

| FIG. 21A |
|---|
| FIG. 21B |

FIG. 21A

| | Biomass to Biogas | | | | Biogas to Fuel | | | |
|---|---|---|---|---|---|---|---|---|
| | In | | Out | | In | | Out | |
| Mass | MSW | 62.7 t/h | CH$_4$ | 23 t/h | CH$_4$ | 23 t/h | H$_2$O | 26.46 t/h |
| | H$_2$O | 340 t/h | H$_2$O | 340 t/h | H$_2$O | 5.75 t/h | N$_2$ | 1.89 t/h |
| | Inoculum | 125 t/h | RB | 76.3 t/h | O$_2$ | 41.16 t/h | H$_2$ | 1.97 t/h |
| | | | CO$_2$ | 88.4 t/h | N$_2$ | 1.89 t/h | C$_2$H$_2$ | 1.64 t/h |
| | | | | | H$_2$ | 0.59 t/h | C$_2$H$_4$ | 1.14 t/h |
| | | | | | | | CO | 12.71 t/h |
| | | | | | | | CO$_2$ | 13.32 t/h |
| | | | | | | | Coke | 0.14 t/h |
| | | | | | | | Biofuel | 6.58 t/h |
| Total Mass | 527.7 t/h | | 527.7 t/h | | 72.39 t/h | | 72.39 t/h | |
| Energy | | | | | 4.7 GJ/h | | 0 GJ/h | |

*FIG. 21B*

INTEGRATED BIOFUEL PRODUCTION SYSTEM

RELATED APPLICATIONS

This application is a continuation-in-part of U.S. patent application Ser. No. 12/118,484, filed May 9, 2008, entitled "BIOFUEL PROCESSING SYSTEM," which claims priority from U.S. Provisional Patent Application Ser. No. 60/917,467, filed May 11, 2007, entitled "BIOFUEL PROCESSING SYSTEM." U.S. Patent Application No. 60/917,467 and Ser. No. 12/118,48 are both hereby incorporated by reference in their entirety.

TECHNICAL FIELD OF THE DISCLOSURE

This disclosure generally relates to biofuels, and more particularly, to integrated systems and methods for converting biomass to biofuels.

BACKGROUND OF THE INVENTION

Biological matter that has been converted to liquefied fuel is generally referred to as biofuel. Biofuel processes that create these biofuels typically use biological processing methods that produce alcohols, such as ethanol. Although these alcohols may have relatively high octane ratings, they have several disadvantages. For example, alcohols have a relatively lower energy density than other hydrocarbons, such as gasoline. Their relatively strong polarity increases the vapor pressure of fuels when added as a constituent such that air pollution is increased. Alcohols also have a tendency to absorb water. This may be problematic when shipping low-molecular-weight alcohols, such as ethanol, in common-carrier pipelines that may contain water. Ethanol is also corrosive, and thus may damage pipelines or dissolve fiberglass fuel tanks. Additionally, because ethanol is miscible with both water and organics, ethanol spills can result in the transport of benzene, toluene, xylene, etc. into the water supply. Finally, it is difficult to extinguish ethanol fires, and fire fighters need additional training and equipment to address this danger.

SUMMARY OF THE INVENTION

Certain embodiment disclose methods and systems for the conversion of biomass to liquid fuels, such as those suitable for powering internal combustion engines, e.g. gasoline, jet engines, e.g. Jet-A, and industrial boilers. Certain methods and systems described herein may benefit from the symbiotic use of matter and energy converted by one subsystem to increase the overall efficiency of the entire system.

According to one embodiment, a biofuel processing system includes a biomass conversion subsystem, a gasification subsystem, and a fuel conversion subsystem. The biomass conversion subsystem uses a biological process to create alcohol, methane, or mixtures thereof from a biomass while producing some amount of residual biomass. The gasification subsystem generates carbon monoxide and hydrogen while producing thermal energy. The thermal energy is captured and used to heat processes in the biomass conversion subsystem and/or the fuel conversion subsystem. Ultimately the fuel conversion subsystem produces a mixture of liquid hydrocarbons (e.g. gasoline) from the alcohols or the methane, or mixtures thereof.

According to another embodiment, a biofuel processing system includes a biomass conversion subsystem, a pyrolysis subsystem, and a fuel conversion subsystem. The biomass conversion subsystem uses a biological process to create alcohol, methane, or mixtures thereof from a biomass while producing some amount of residual biomass. The pyrolysis subsystem generates hydrocarbon gasses (pyrolysis gasses) and/or pyrolysis oil from the residual biomass. Ultimately the fuel conversion subsystem produces a mixture of liquid hydrocarbons (e.g. gasoline) from the alcohols, the methane, or mixtures thereof using the hydrocarbon gasses produced from the pyrolysis of the residual biomass. According to another embodiment, a biofuel conversion process comprises converting biomass to alcohol, methane, or mixtures thereof and residual biomass, thermalyzing the residual biomass to produce hydrocarbon gasses, carbon monoxide, hydrogen, or mixtures thereof, and synthesizing a biofuel from the alcohol, methane, or mixtures thereof and the hydrocarbon gasses, carbon monoxide, hydrogen, or mixtures thereof. The biofuel production process benefits from the symbiotic use of residual biomass and energy to create process gasses needed for the synthesis of biofuels and to provide heat for the conversion of biomass to a stream of hydrocarbons as well as the synthesis of biofuels.

Other embodiments may comprise a combination of different biomass conversion processes, and/or a combination of thermalyzing processes, and/or a combination of fuel synthesis processes. Such embodiments may comprise multiple biomass conversion processes, such as anaerobic fermentation and anaerobic digestion, and then combine the residual biomass for a single pyrolysis process, to produce hydrocarbon gasses which are synthesized into fuels in combination with the products from the multiple biomass conversion processes.

Some embodiments of the disclosure provide numerous technical advantages. Some embodiments may benefit from some, none, or all of these advantages. For example, according to one embodiment, a fuel may be produced having a relatively high energy density that may be generally compatible with commonly used fuels, such as gasoline or kerosene. The biomass processing system includes a number of processing steps that may enable conversion of a relatively large portion of the energy content of the biomass ingredient. The efficiency of the conversion process may be enhanced by utilizing heat and/or mass from one process as an ingredient to another process. Thus, the biomass processing system may enable a relatively high degree of yield in relation to the amount of biomass introduced into the biofuel processing system. Other technical advantages may be readily ascertained by one of ordinary skill in the art.

BRIEF DESCRIPTION OF THE DRAWINGS

A more complete understanding of embodiments of the disclosure will be apparent from the detailed description taken in conjunction with the accompanying drawings in which:

FIG. 4 shows the suitability of various feedstocks for the methods of embodiments of the present disclosure;

FIG. 11 shows a fuel conversion subsystem used to convert methane and hydrogen to a biofuel;

FIG. 12 shows a fuel conversion subsystem used to convert alcohol, methane and hydrogen to a biofuel;

FIG. 17 shows mass and energy inputs and outputs for the biomass conversion, thermalysis, and fuel synthesis processes of integrated biofuel processing system shown in FIG. 16;

FIG. 19 shows mass and energy inputs and outputs for the biomass conversion, thermalysis, and fuel synthesis processes of the integrated biofuel processing system shown in FIG. 17;

FIG. 21 shows mass and energy inputs and outputs for the biomass conversion, thermalysis, and fuel synthesis processes of the integrated biofuel processing system shown in FIG. 19;

DETAILED DESCRIPTION

Before any embodiments of the invention are described in detail, it is to be understood that the invention is not limited in its application to the details of construction and the arrangement of components set forth in the following description. The invention is capable of other embodiments and of being practiced or of being carried out in various ways. Also it is to be understood that the phraseology and terminology used herein is for the purpose of description and should not be regarded as limiting. The use of "including," "comprising," or "having" and variations thereof in the Detailed Description, but not the Claims, is meant to encompass the items listed thereafter and equivalents thereof, as well as additional items.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the invention unless otherwise claimed. No language in the specification should be construed as indicating any nonclaimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion in the such references states what their respective authors assert, and the applicant reserves the right to challenge the accuracy and pertinency of any of the documents cited herein.

Figure 3:
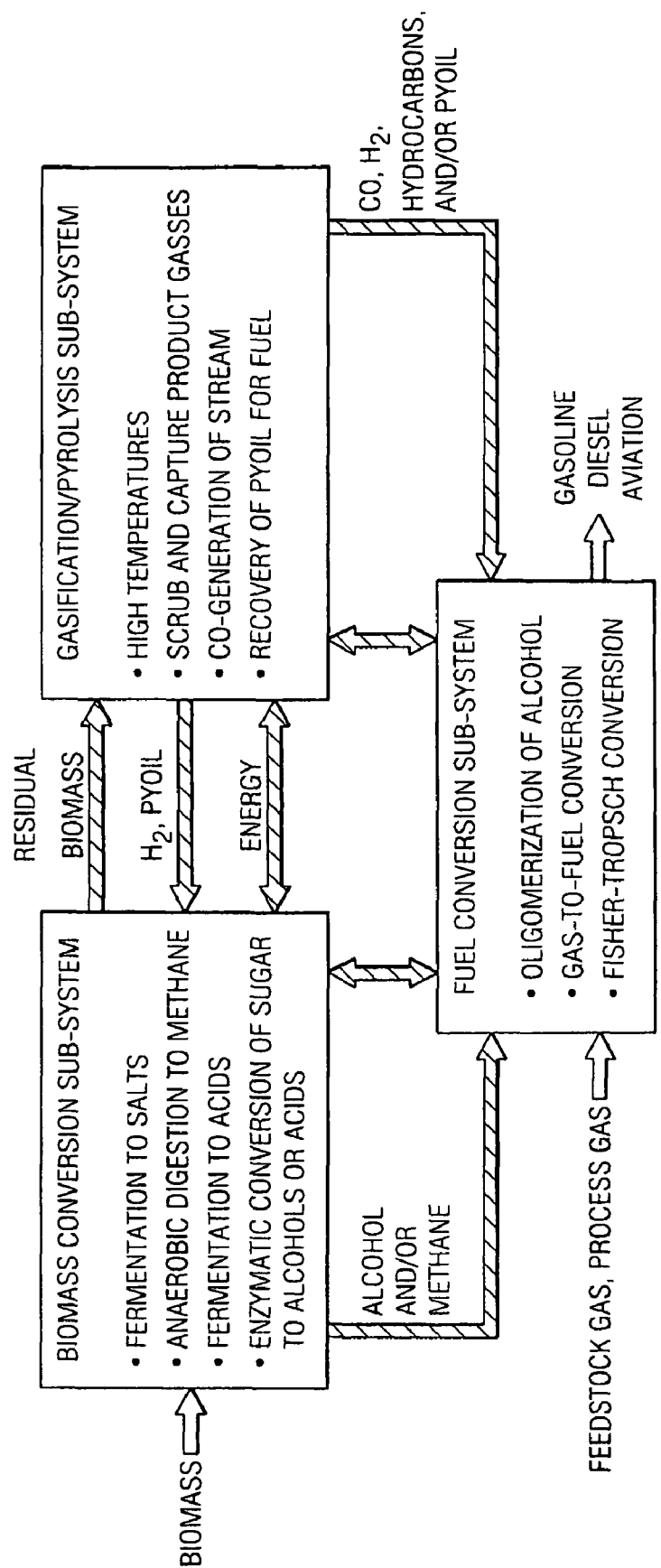
FIG. 3 is a schematic overview of a biofuel processing system according to an embodiment of the present disclosure.

An overview of the methods of certain embodiments is shown in FIG. 3. Integrated biofuel production systems of certain embodiments may be visualized as at least three interdependent subsystems symbiotically sharing waste materials and/or thermal energy that has traditionally been discarded. The three subsystems are Biomass Conversion, Gasification/Pyrolysis, and Fuel Conversion. (In some figures and descriptions, the three subsystems are referred to as "Biomass Conversion System," "Gasifier and/or Pyrolyzer," and "Synthetic Fuel Creation System," however these systems are equivalent to the subsystems bearing the same or similar names.) While certain embodiments of the production systems may be conceptualized as three interdependent subsystems, a given embodiment may not have readily recognizable subsystems because of the need to interconnect sinks and sources of materials and thermal energy in order to maximize efficiency. However, the interconnections allow certain embodiments of the biofuel production systems to use materials and thermal energy most efficiently, thus making it possible to produce more liquid fuel from less biomass, while using less external energy to drive the process.

Certain embodiments of the biomass conversion subsystems may entail any of a number of known methods suitable for converting biomass into methane or an alcohol and residual biomass. Such methods may include, but need not be limited to, fermenting biomass to carboxylic acid salts (and ultimately secondary alcohols), anaerobic digestion of biomass to produce biogas or acetic acids, fermentation of biomass to acids or alcohols, and enzymatic conversion of sugars to alcohols or acids. Certain methods need not be limited to a singular biomass conversion system, as it may be beneficial to incorporate more than one type of biomass conversion system into a given biofuel processing system.

Certain embodiments of the gasification/pyrolysis subsystems may entail any number of known methods suitable for converting residual biomass to heat and product gases by thermalyzing the residual biomass at high temperatures. Certain gasification and pyrolysis processes of the disclosure may alternatively be referred to generally as thermolysis processes, i.e., the breaking of chemical bonds with heat. Pyrolysis typically involves the conversion of residual biomass to pyrolysis gas and/or pyrolysis oil and char, by the thermal decomposition of the residual biomass in the absence of oxygen. Pyrolysis typically takes place at a temperature of 300-600° C., preferable at a temperature of 450-550° C. The pyrolysis gas may comprise a mixture of alkanes and alkenes, such as ethane, ethylene, propane, propylene, with some residual decomposition gases, including amines, sulfides, and halides. The pyrolysis gas may be directly injected into the fuel conversion subsystem for conversion to hydrocarbon fuel products, or the pyrolysis gas may be combusted to produce thermal energy. In alternate embodiments, the pyrolysis reactor may be configured to produce predominantly pyrolysis oil, or a mixture of pyrolysis oil and gas. The pyrolysis oil comprises a mixture of long chain hydrocarbons, and oxygenated hydrocarbons (e.g. aldehydes, ketones, and alcohols) that can be used as a fuel source for processing steps needing external energy inputs, such as thermal conversion of carboxylic acid salts to ketones. In some embodiments, the pyrolysis oil may be converted to hydrocarbon fuels using known methods.

Certain embodiments of the asification typically may involve the conversion of residual biomass to a mixture of carbon monoxide and hydrogen, generally known as "syn gas." In the gasification process, residual biomass is partially combusted in the presence of oxygen at a temperature of 800-1400° C., preferably at a temperature of 950-1150° C. Because of the higher temperatures and the presence of oxygen, the residual biomass is converted almost entirely to a clean syn gas that can be converted to fuel with a Fisher-Tropsch process. Alternatively, the hydrogen and carbon monoxide may be separated, allowing the hydrogen to serve as a feed gas for other processes, such as the hydrogenation of ketones to secondary alcohols, while the CO is captured to be used in other industrial processes. It is also known to combine CO with steam to produce additional hydrogen gas and carbon dioxide via the water gas shift reaction. It is possible to react the syn gas with steam, without pretreatment, to produce additional hydrogen. If the syn gas is not fed into a Fisher-Tropsch reactor, the syn gas will typically pass through one or more heat exchangers prior to being separated. In this way the thermal energy produced in the gasification process can be captured and used to decrease the amount of energy that must be input for high temperature processes such as the thermal conversion of carboxylic acids to ketones and the oligomerization of alcohols to liquid hydrocarbons to be used as fuels.

A variety of products may be produced from the biomass conversion subsystem(s) and/or the gasification/pyrolysis subsystem. In embodiments where methane and/or other hydrocarbon gasses are produced, a gas-to-liquid (GTL) hydrocarbon conversion process will be most suitable. Such systems are known to those of skill in the art, and have been commercialized by Synfuels International (Dallas, Tex.). The GTL systems typically comprise a four step process, and are able to produce gasoline, diesel and aviation fuels from low-molecular weight starting materials including, but not limited to, as methane, ethane, propane, and butane. In other embodiments where alcohols are produced from the biomass conversion subsystem, it will be suitable to convert the alcohols to liquid hydrocarbons with a combined dehydration and oligomerization process that is known to those of skill in the art. Such dehydration/oligomerization processes typically involve converting the alcohols at high temperature and pressure in the presence of a zeolite catalyst. In other embodiments it is possible to simultaneously convert multiple hydrocarbon streams including methane, hydrocarbon gases, and alcohols into liquid hydrocarbon fuels. For larger-scale embodiments, it may be desirable to incorporate a Fisher-Tropsch reactor to convert the syn gas (from gasification) to liquid hydrocarbon fuels. Fisher-Tropsch conversion of syn gas to fuel is known to those of skill in the art, and commercial reactors have been constructed by Syntroleum Corporation (Tulsa, Okla.).

While many embodiments gasify and/or pyrolyze residual biomass, it may be also advantageous to gasify and/or pyrolyze raw (virgin) biomass to produce heat and/or production gasses for use in the fuel conversion subsystem. The gasification and/or pyrolysis or raw biomass may be used to supplement the heat and production gasses produced through the gasification and/or pyrolysis of residual biomass. Additionally, because anaerobic digestion and fermentation processes can require a few weeks of digestion time, it may be necessary to gasify and/or pyrolyze raw biomass directly to mixed hydrocarbon gasses to maintain production levels during start-up, or in the event the anaerobic microorganism population unexpectedly collapses.

The interconnections between subsystems of the biofuel processing system are depicted with hashed arrows in FIG. 3. Some of the interconnections represent the transport of materials, and some of the interconnections represent the transport of energy. The interconnections may involve the transfer of residual biomass from the biomass conversion subsystem to the gasification/pyrolysis subsystem, the transfer of alcohol and methane to the fuel conversion subsystem, the transfer of process gasses from the gasification/pyrolysis subsystem to the fuel conversion subsystem or the biomass conversion subsystem, and, optionally the transfer of pyrolysis oil from the gasification/pyrolysis subsystem to the biomass conversion subsystem or the fuel conversion subsystem where the pyrolysis oil is burned to provide thermal energy for one or more processes.

FIG. 3 additionally depicts the transfer of thermal energy between the interdependent subsystems. Such transfer may include, but need not be limited to, the recovery of "waste heat" from the gasification/pyrolysis subsystem to meet the heating needs of the biomass conversion system (e.g. heating an anaerobic digester), or using products of the biomass conversion subsystem as a quench in one or more stages of the fuel conversion subsystem. Thermal energy may be recovered from a number of other process steps present in the biomass conversion, gasification/pyrolysis, or fuel conversion subsystems.

One of skill in the art appreciates that capturing and transporting thermal energy as well as residual biomass and gasses may require transfer systems that are not shown in FIG. 3. For example, a number of conveyors and pumps will be needed to move materials and thermal loads between subsystems. Materials handling equipment, such as cleated rubber belt conveyors, are known to those of skill in the art, and is available from any number of materials handling companies, such as Kornylack Corp. (Hamilton, Ohio). Heat transfer systems may rely on pressurized water or other known heat-transfer fluids (e.g., Dow-Therm) to recover the heat and to serve as a heat-transfer medium between the various components of the subsystems. Heat transfer systems appropriate for use in certain embodiments are known to those of skill in the art, and are available from companies, such as, but not limited to, Met-Pro Corp. (Harleysville, Pa. In some embodiments, it may be beneficial to produce steam from excess thermal energy, which may be used for both heating processes and to provide electrical energy (by driving a turbine) to power the transfer systems.

While it is possible to produce electricity to drive the heat and material transfer processes with steam, in many cases it is more efficient to use the thermal energy produced by the subsystems for heating rather than electrical production. Optimally, the heat and material transfer systems can be powered from other renewable energy sources amenable to the production of electricity, such as a wind turbines, solar panels, or a biogas-powered electrical generators. However, the transfer systems can also be powered with electricity from the local power grid.

FIG. 3 additionally depicts process gas, feedstock gas, and alcohol inputs that may be used to maximize the production of hydrocarbon liquids to be used as fuels. In some cases, depending upon spot market prices for process gasses (such as hydrogen) and alcohols (such as ethanol) it may be economically advantageous to replace the interdependent processes with these inputs. For example, it may be beneficial to buy ethanol on the open market to feed into the oligomerization reactor used to convert alcohols to liquid hydrocarbon fuels. It may also be beneficial to steam reform natural gas to produce hydrogen to be used in the various hydrogenation steps. Of course, it may also be beneficial to steam reform renewable sources of methane, such as landfill gas or biogas from a digester in order to produce hydrogen to be used in the various hydrogenation steps.

As used herein, the term "hydrocarbon" refers to any molecule consisting of carbon and hydrogen in any combination. As such, "hydrocarbon" includes straight-chain, branched, and cyclic alkanes, alkenes, alkynes, and aromatics. Of particular importance to the certain embodiments are hydrocarbon gasses, e.g. those hydrocarbons with low vapor pressures, such as short chain alkanes, alkenes, and alkynes.

As used herein, the term "alcohol" and "alcohols" refers to any of a number of carbon-containing molecules having one or more singly-bonded hydroxyl (OH) groups. The term "alcohol" encompasses both primary (e.g. OH on terminal carbon) and secondary (e.g. OH not on terminal carbon) alcohols. The number of carbon atoms in the alcohols of certain embodiments is typically less than 10, more typically less than 6, however longer-chain alcohols may be produced in smaller amounts and incorporated into the systems of embodiments. Alcohols suitable for the particular embodiments include, but are not limited to, methanol, ethanol, n-propanol, isopropanol, n-butanol, and isobutanol.

As used herein, the term "ketones" refers to any of a number of carbon containing molecules having a doubly-bonded oxygen to a secondary (e.g. non-terminal) carbon. Ketones of certain embodiments typically have less than 10, more typically less than 6, carbon atoms in the molecule, however longer-chain and branched ketones may be produced in smaller amounts and incorporated into the embodiments of systems. Ketones suitable for particular embodiments include, but need not be limited to, propanone (acetone), butanone, and pentanone.

As used herein, the term "carboxylic acids" refers to any of a number of carbon containing molecules having an organic acid group (COOH). Carboxylic acids of certain embodiments typically have less than 10, more typically less than 6, carbon atoms in the molecule, however longer-chain carboxylic acids may be produced in smaller amounts and incorporated into the embodiments of systems. Carboxylic acids suitable for the particular embodiments include, but are not limited to, methanoic acid (formic acid), ethanoic acid (acetic acid), propanoic acid, and butanoic acid (butyric acid).

Furthermore, it is understood by those of skill in the art that chemical compounds are identical regardless of their origin. For example, methane ($CH_4$) produced from the anaerobic digestion of animal manure is identical to methane recovered from landfill gas, which is identical to methane in natural gas, etc. Thus it is not necessary to keep track of a given source of methane to be used in a particular process, as regardless of the source, the methane is identical. Any use of "additional," or "supplemental," or "second" to modify a chemical compound is simply a means for tracking the origin of the chemical compound for mass balance calculations and has no bearing on the properties of the compound.

In certain embodiments, the methods and systems may enable the efficient production of liquid hydrocarbon fuels from biomass. Hydrocarbon fuels created by embodiments may include, but need not be limited to gasoline, diesel, kerosene, jet/aviation fuel, and light heating oils, wherein these fuels meet the various standards set out by ASTM International and the U.S. E.P.A. In most cases, however, the fuels will not contain sulfur compounds and heavy metals at the levels found in conventional petroleum fuels.

In certain embodiments, the systems and methods may also allow for the production of organic chemicals such as olefins, paraffins, aromatics, and naphthenes. Of particular value are chemicals that may be used as feedstocks to the petrochemical industry such as ethylene, acetylene, benzene, cyclohexene, xylene, toluene, ethylbenzene, etc. By varying the temperature, pressure, and catalysts of the fuel conversion subsystem, it may be possible to optionally produce fuel or feedstocks depending upon the market price for a given fuel or feedstock chemical.

Biomass suitable for use with the systems and methods of certain embodiments may include, but need not be limited to, animal manures, kitchen waste, food processing waste, beverage waste, thin and whole stillage, wet distillers grain, raw human sewage, municipal solid waste, treated sewage sludges, fats, oils, greases, meat packing waste, paunche, tallows, processed lignocellulosic waste, pulp and paper sludges, wood wastes, landfill gas, digester gas, energy crops (cane, sorghum, miscanthus, switch grass), timber (poplar, aspen, willow, alder), crop residues (corn stover, wheat or rice straw, palm), algae, diatoms, seaweed, and other discarded vegetation including municipal grass and timber wastes. Municipal solid waste may include items that are not of (recent) biological origin but, nonetheless, may be processed by the embodiments of the systems. Such non-biological materials may include, but need not be limited to, plastics, solvents, used motor oil, and construction debris. References to "biomass," "raw biomass," "virgin biomass," "a first biomass," or "a second biomass" are intended to encompass any of the biomass described above.

Residual biomass typically comprises the solid materials that remain after biomass has undergone a biomass conversion process described herein. Residual biomass typically has a reduced cellulose content in comparison to virgin biomass because the biomass conversion process preferentially results in the degradation of cellulose. A biomass conversion process typically does not greatly affect the lignin content of a biomass, however. As used herein, it is intended that "residual biomass," "a first residual biomass," or "a second residual biomass" all refer to remnant materials resulting from the conversion of biomass with processes described herein, or processes similar to those described herein.

FIG. 4 describes the suitability of various feedstocks to the subsystems described herein. In particular, the GTL fuel conversion subsystem is very robust in being able to produce liquid hydrocarbon fuels from a number of biomass conversion process products (e.g., methane, hydrocarbon gasses, and pyrolysis oil). While it is not explicitly noted in FIG. 4, it is to be understood that the suitability of residual biomass from a particular feedstock for gasification or pyrolysis is, for the most part, similar to the suitability of the virgin biomass.

Figure 5:
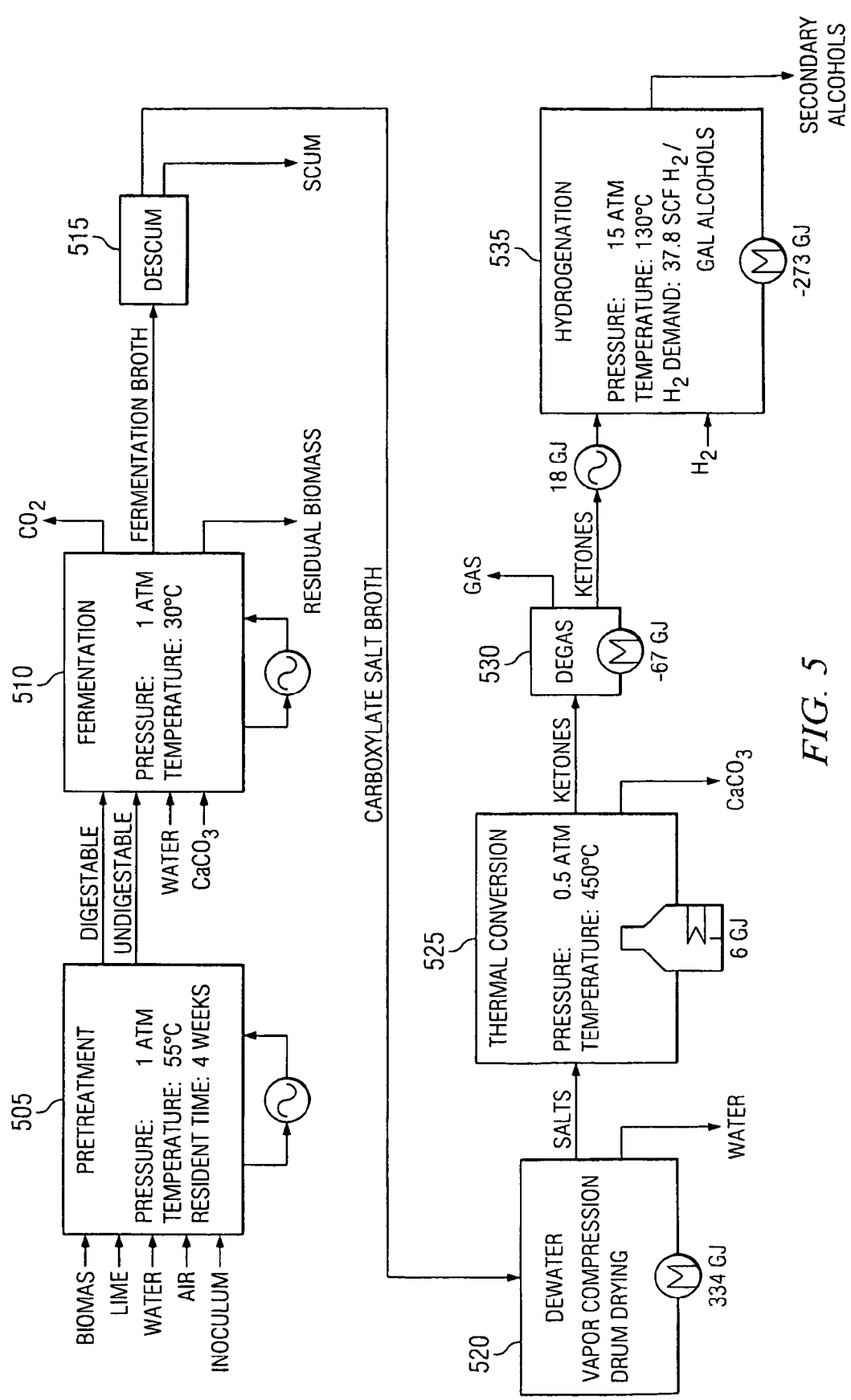
FIG. 5 shows a biomass conversion subsystem in which biomass is converted to carboxylic acid salts and residual biomass, and the carboxylic acid salts are further converted ketones.

One method for the conversion of biomass to alcohol and residual biomass involves suppressing methanogenic bacteria during the anaerobic (e.g., low oxygen) fermentation of biomass to produce carboxylic acids. This method, depicted in FIG. 5 is known to those of skill in the art and is described in U.S. Pat. Nos. 5,693,296, 5,865,898, 5,874,263, 6,043,392, and U.S. Patent Application Publications Nos. 2004/0168960, 2004/0171136, 2006/0188980, 2006/0024801, 2007/0014895, and 2008/0121359. The method can be described generally as pretreatment of the biomass and then fermentation under controlled conditions. The biomass first undergoes pretreatment 505 where it is mixed with lime and optionally air or oxygen, which facilitates digestion of the biomass. The lime-treated biomass is slowly added to a fermentor 510 (having a bottom collector) where anaerobic organisms convert the biomass to organic acids over a period of several weeks. A methanogen inhibitor (e.g., iodoform0 may be added to suppress methane formation. Fermentor 510 is typically maintained at a temperature between 20-80° C. The anaerobic organisms may be, for example, a mixed culture obtained from cattle rumen, soil, compost, or anaerobic sewage digesters. The fermentation process produces a mixture of carboxylic acids, but mainly acetic acid with lesser amounts of propionic and butyric acids. The ratio of the various carboxylic acids depends on factors such as the microbial population, the pH, and temperature. Some of the carboxylic acids are neutralized by residual calcium to create carboxylic salts. However, additional lime and/or calcium carbonate is typically added along with water to assure the complete conversion of carboxylic acids to carboxylate salts as the fermentation process continues. Generally, a pH near 6.2 is preferred, but the pH can range from about 5.5 to about 7.0.

As the added water trickles through the biomass, the carboxylic acid salts are dissolved, resulting in a carboxylate salt solution. The carboxylate salt solution is collected from the bottom of the fermentor, cleaned and descummed 515. The carboxylate salts are then removed from the solution (dewatered) 520 with a known technique such as evaporation or evaporation in conjunction with chemical concentration. In particular, the separation methods described in U.S. Pat. Nos. 5,962,307, 5,986,133, 6,395,926, 6,478,965, and 7,251,944 and U.S. Patent Application Publication No. 2005/0072662, are particularly well suited for the separation of carboxylate salts from the solution.

Once the solid carboxylate salts are isolated, they may be converted to ketones using a known thermal conversion process 525. Such processes are described in U.S. Pat. Nos. 5,969,189 and 6,262,313 and U.S. Patent Application Publication No. 2005/0061493. In brief, dried carboxylate salts are heated to approximately 400-500° C. in a reduced atmosphere (0.5 atm) in the presence of heat transfer agents, such as Pyrex beads, to produce ketone vapors that are drawn off and condensed. The condensed ketone vapors may be subsequently converted to secondary alcohols in a hydrogenation process 535 in which the ketones are reacted with high pressure hydrogen gas at moderate temperatures, typically around 130° C., in the presence of a hydrogenation catalyst. In some embodiments, it may be commercially worthwhile to draw off a portion of the ketones for sale as bulk chemicals, e.g. solvents.

Figure 6:
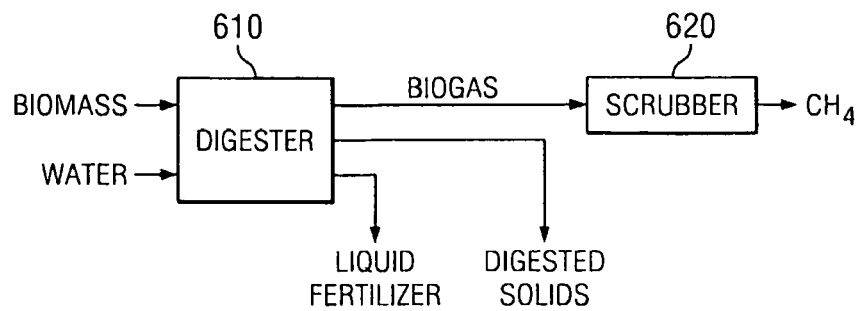
FIG. 6 shows a biomass conversion subsystem in which biomass is converted to methane and residual biomass.

A second method of biomass conversion, simple anaerobic digestion is depicted in FIG. 6. An anaerobic digester 610 typically takes the form of a covered, heated pit, however many different embodiments are known. For example cow manure may be collected with water and digested until completion in a single tank, or the waste and water may be arranged so that it will flow slowly through a tunnel-like structure, for example, until completion. Advanced reactors such as induced blanket reactors (IBR) are also known. In all anaerobic processes, the oxygen content and temperature of the waste are carefully controlled to maximize the production of biogas, which contains mostly methane (50-75%) and carbon dioxide (20-30%) along with trace amounts of nitrogen, hydrogen, oxygen and hydrogen sulfide. The biogas is recovered and scrubbed in a scrubber 620 to remove the sulfides, and the remaining gas may be fed directly into the fuel conversion subsystem. In most cases, it is possible to remove the liquid component from the digested biomass at the conclusion of digestion, thus leaving residual biomass that may be used for the gasification or pyrolysis subsystems. The liquid component is typically high in nitrogen, and has independent value as a fertilizer, which may be used for the production of additional animal feed or biomass feedstocks.

Anaerobic digesters 610 are typically constructed on site, and several companies install and manage digesters. For example, GHD Incorporated (Chilton, Wis.) installs and manages digesters for conversion of agricultural by-products to bio-gas. Those of skill in the art are also familiar with modifications necessary to anaerobically digest alternative feedstocks, such as those shown in FIG. 4.

Figure 7:
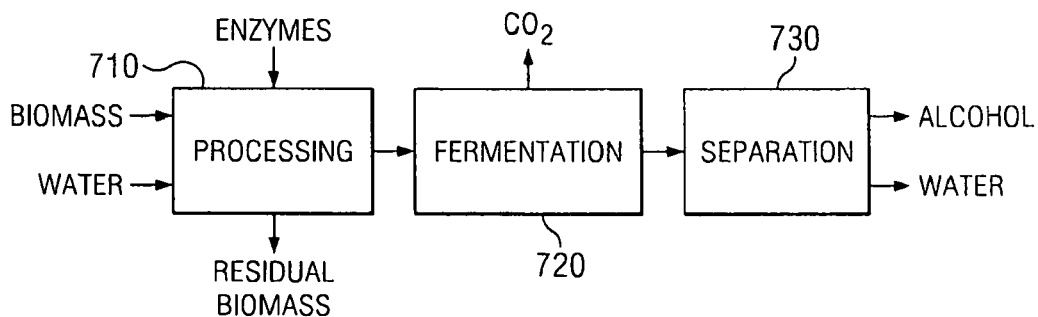
FIG. 7 shows a biomass conversion subsystem in which biomass is converted to alcohol and residual biomass.

A third method of biomass conversion may comprise conventional fermentation of biomass or grains such as corn, rice, wheat, etc. These methods are well known to those of skill in the art, and are represented by the schematic diagram shown in FIG. 7. For example, "conventional" ethanol from corn mash is practiced on an industrial scale in many countries. Conventional ethanol production facilities may be built and managed by companies such as FEECO International (Green Bay, Wis.). The fermentation process consists essentially of a processing step 710, a fermentation step 720, and a separation (distillation) step 730, as shown in FIG. 7. In processing step 710 the biomass or grains are crushed or ground or enzymatically treated to make the sugars in the feedstock more accessible for the microorganism (e.g., yeast) that will ferment the sugars to alcohol. It is also known to acid hydrolyze cellulosic materials to produce free sugars.

In the fermentation step 720 a mixture of water and processed feedstocks are typically allowed to ferment at elevated temperatures until the alcohol content reaches approximately 15%. The fermentation process 720 typically takes 40 to 50 hours. The resultant mixture of water, feedstock and alcohol is then separated 730 to produce a clean stream of alcohol that can be fed to the fuel conversion subsystem. Typically, the fermentation process results in the production of ethanol, however methods for the production of butanol from biomass and/or grains are known.

Figure 2E:
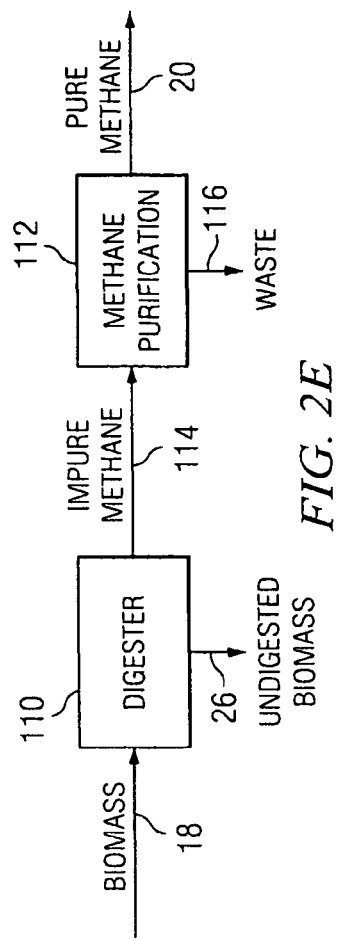
FIG. 2E is another embodiment of the biomass conversion subsystem that converts biomass to methane.
Figure 2A:
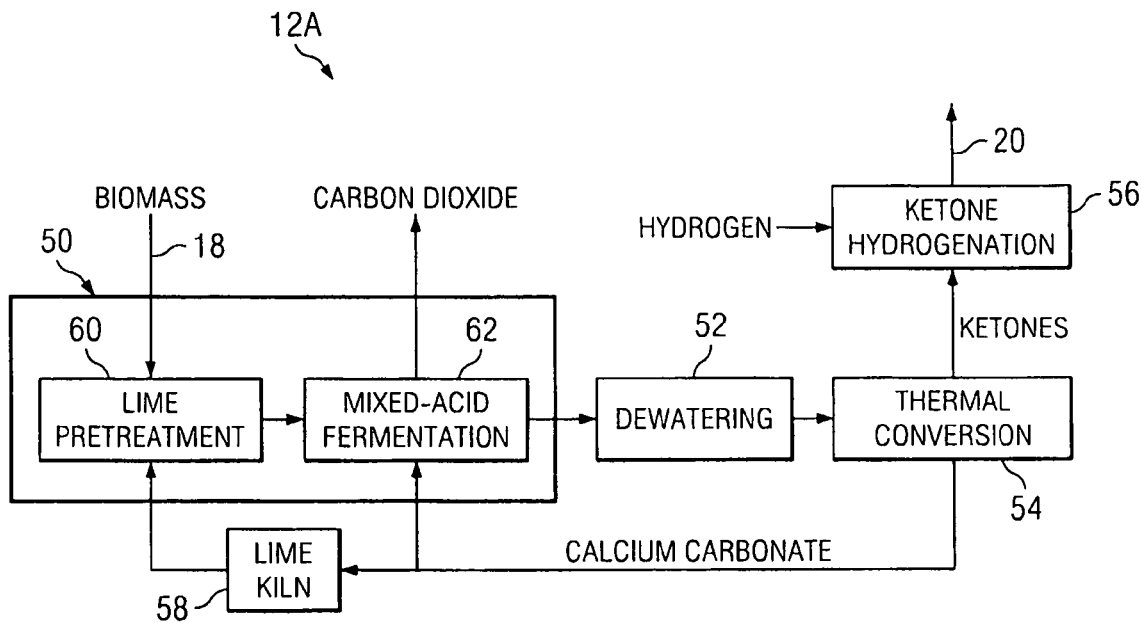
FIG. 2A is one embodiment of a biomass conversion subsystem that converts biomass to secondary alcohols.

FIG. 2A shows another embodiment of a biomass conversion system 12A that may be used to generate methane and/or alcohol 20 including secondary alcohols. Biomass conversion system 12A generally includes a lime treatment section 50, a dewatering section 52, a thermal conversion section 54, a ketone hydrogenation section 56, and a lime kiln 58 coupled as shown. Lime treatment section 50 includes a lime pretreatment portion 60 and a mixed-acid fermentation portion 62. Lime pretreatment portion 60 mixes the incoming biomass feed 18 with lime from lime kiln 58 to enhance its digestibility. The lime-treated biomass is then fermented in mixed-acid fermentation section 62 using a mixed-culture of microorganisms that produces a mixture of carboxylic acids, such as acetic acid, propionic acid, and/or butyric acid. Calcium carbonate may be added to mixed-acid fermentation portion 62 to neutralize the acids to form their corresponding carboxylate salts, such as calcium acetate, calcium propionate, and calcium butyrate. After fermentation, these salts may be removed from the fermentation broth in dewatering section 52 to produce dried calcium carboxylate salts. The dried carboxylate salts are then converted thermally to ketones in thermal conversion section 54. Ketone hydrogenation section 56 may be used to catalytically hydrogenate the ketones into secondary alcohols, such as isopropanol.

Figure 2B:
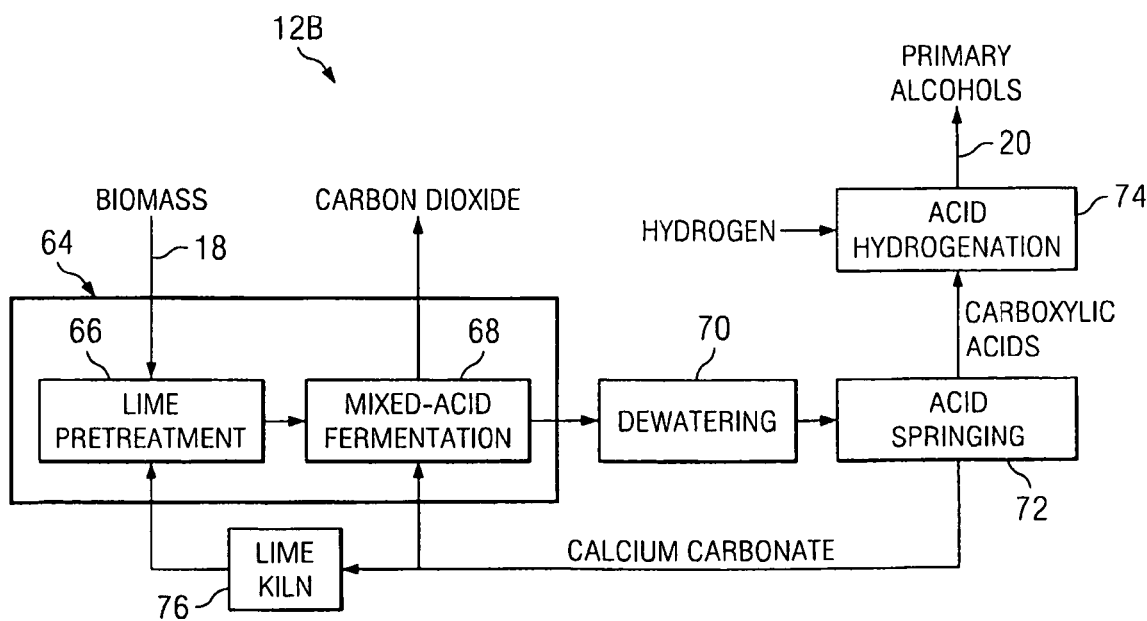
FIG. 2B is another embodiment of the biomass conversion subsystem that converts biomass to primary alcohols.

FIG. 2B shows another embodiment of biomass conversion system 12B that may be used to generate methane and/or alcohol 20 comprising primary alcohols. Biomass conversion system 12B includes a lime treatment section 64 having a lime pretreatment portion 66 and a mixed-acid fermentation portion 68, a dewatering section 70, a acid springing section 72, an acid hydrogenation section 74, and a lime kiln 76 coupled as shown. Lime treatment section 64, dewatering section 70, and lime kiln 76 function in a manner similar to lime treatment section 50, dewatering section 52, and lime kiln 58 of biomass conversion system 12A. Biomass conversion system 12B differs, however, in that acid springing section 72 springs carboxylic acids from the concentrated carboxylate salt solution. In the acid springing step, carboxylate salts react with a tertiary amine and carbon dioxide causing calcium carbonate to precipitate while the amine carboxylates remains in solution. Then, in a reactive distillation column, the amine carboxylates are thermally cracked into tertiary amines and carboxylic acid. The tertiary amine and calcium carbonate are recycled within the process consuming relatively few chemicals. The resulting acids react with a high-molecular-weight alcohol, such as heptanol, to form the corresponding esters. In the acid hydrogenation section 74, the esters are hydrogenated to form primary alcohols. The high molecular-weight alcohol is recovered by distillation and the low-molecular-weight primary alcohols are transported to synthetic fuel creation system 16.

Figure 2C:
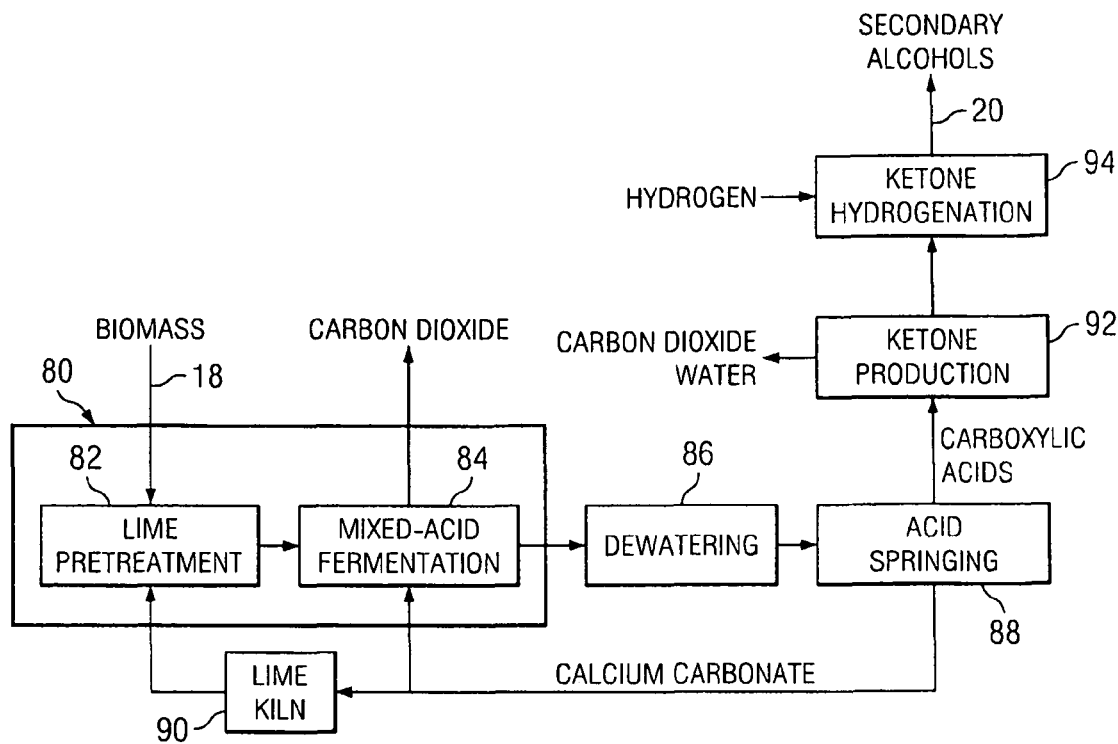
FIG. 2C is another embodiment of the biomass conversion subsystem that converts biomass to secondary alcohols.

FIG. 2C shows another embodiment of biomass conversion system 12C that may convert the biomass to methane and/or alcohol 20 comprising secondary alcohols. Biomass conversion system 12B includes a lime treatment section 80 having a lime pretreatment portion 82 and a mixed-acid fermentation portion 84, a dewatering section 86, an acid springing section 88, and a lime kiln 90 similarly to biomass conversion system 12B of FIG. 2B. Biomass conversion system 12C differs, however, in that it includes a ketone production section 92 and a ketone hydrogenation section 94. Ketone production section 92 catalytically converts carboxylic acids into ketones, which are subsequently hydrogenated by ketone hydrogenation section 94 into secondary alcohols that are converted to fuels in synthetic fuel creation system 16.

Figure 2D:
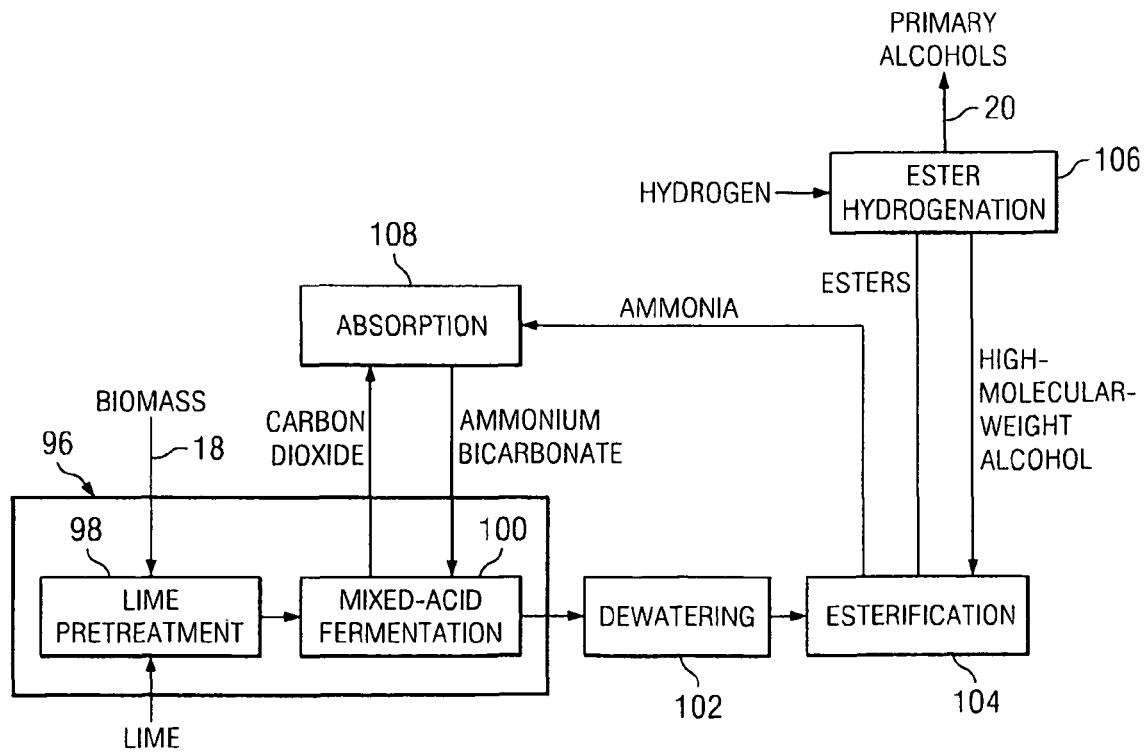
FIG. 2D is another embodiment of the biomass conversion subsystem that converts biomass to primary alcohols.

FIG. 2D shows another embodiment of biomass conversion system 12D that may convert biomass feed 18 to methane and/or alcohol 20 comprising primary alcohols. Biomass conversion system 12D includes a lime treatment section 96 having a lime pretreatment portion 98 and a mixed-acid fermentation portion 100, a dewatering section 102, an esterification section 104, an ester hydrogenation section 106, and an absorption section 108. Lime pretreatment portion 98 mixes the incoming biomass feed 18 with lime to enhance its digestibility. The pretreated biomass is then fed to mixed-acid fermentation section 100 where a mixed culture of microorganisms produces mixed acids that are neutralized with an ammonium bicarbonate stream from absorption section 108. The ammonium salts are concentrated and then esterified in esterificaton section 104 by adding a high-molecular-weight alcohol, which releases ammonia. The ammonia is recovered in absorber section 108 where it reacts with carbon dioxide to produce ammonium bicarbonate. The esters are hydrogenated to produce primary alcohols. The high-molecular-weight alcohol is recycled in esterification section 104, and the low molecular-weight alcohols are transmitted to synthetic fuel creation system 16. The molecular weight distribution of the alcohols depends upon operating temperatures and the amount of buffer used. Lower temperatures, (e.g., 40° C.) may favor higher alcohols while higher temperatures (e.g., 55° C.) may favor lower alcohols. Calcium carbonate buffer may favor higher alcohols while ammonium bicarbonate buffer may favor lower alcohols.

FIG. 2E shows another embodiment of biomass conversion system 12E that may convert biomass feed 18 to methane and/or alcohol 20 comprising relatively pure methane. Biomass conversion system 12E generally includes a digester 110 and a methane purification process 112 as shown. Digester 110 receives biomass stream 18 and produces an impure methane stream 114 and residual biomass stream 26 that may be fed to gasifier 14. Methane purification process 112 filters waste from impure methane stream 114 to methane and/or alcohol 20 including relatively pure methane that is fed to synthetic fuel creation system 16. The waste may be emitted from methane purification process 112 as waste stream 116. This biomass conversion process 12E may avoid the production of any significant amounts of alcohols by producing mainly methane, which may be used by synthetic fuel creation system 16 for the production of high molecular-weight alcohols.

The biomass conversion systems depicted in FIGS. 2A-E, and 5-7 are intended to be illustrative, and are not intended to limit the scope of the invention. Other methods of producing useful feedstocks for the fuel conversion subsystem are also known to those of skill in the art. For example, it is possible to anaerobically digest wastes to produce acids which may be incorporated into the fuel conversion subsystem. Additionally, it is anticipated that new methods for converting biomass to methane or alcohol and residual biomass are likely to be discovered in the near future.

Figure 8:
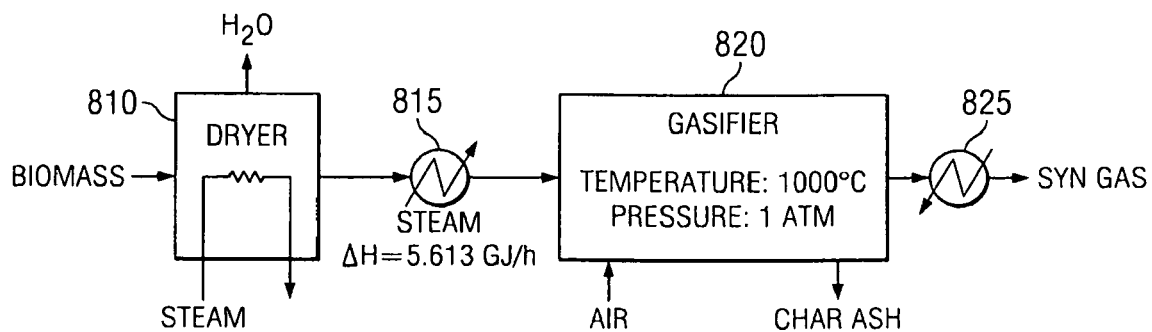
FIG. 8 shows a gasification subsystem configured to gasify residual biomass to CO and $H_2$.

FIG. 8 depicts an exemplary gasification subsystem that may be suitable for incorporation into an embodiment of a biomass conversion system. Residual biomass originating from one or more biomass conversion subsystems is collected and dried in dryer 810 to achieve approximately 10% moisture content. The dried biomass is then preheated using a steam driven heat exchanger 815. The hot, dried, residual biomass is then injected into a gasification reactor 820 where the residual biomass is burned in the presence of air at approximately 1000° C. to produce syn gas and a small amount of char. The resultant syn gas is cooled by a second heat exchanger 825 prior to being scrubbed to remove any residual HCl, $H_2S$, or heavy metals. The thermal energy captured in the second heat exchanger 825 may be circulated to another subsystem of the biomass conversion system, where the thermal energy can be used to preheat other processes, or drive the thermal decomposition of carboxylate salts, for example. Gasification reactors suitable to be used as subsystems for certain embodiments may be obtained from companies such as, but not limited to, TRI Inc. (Baltimore, Md.) and Frontline Bioenergies (Ames, Iowa).

In some cases the syn gas can be converted directly without the need to separate the hydrogen and carbon monoxide. For example syn gas may be fed directly into a Fisher-Tropsch reactor (FIG. 13) and converted into liquid hydrocarbon fuel. For other applications, it may be necessary to separate the hydrogen from the carbon monoxide in order to produce (relatively) pure hydrogen that can be used for high pressure hydrogenation reactions in the presence of catalysts sensitive to carbon monoxide. Methods for separating gas mixtures are known to those of skill in the art, and may include, but need not be limited to, membrane filtration, absorption, and cryogenic separations. Gas separation equipment suitable for use with certain embodiments may be obtained from companies, such as, but not limited to, Praxair, Inc. (Danbury, Conn.).

Figure 9:
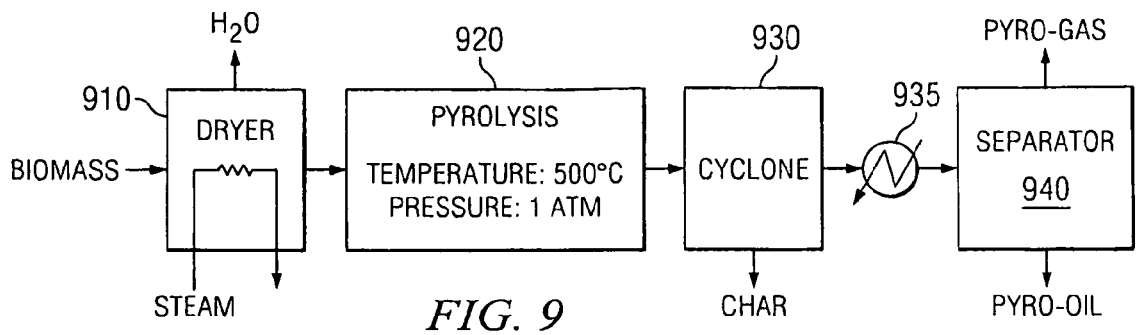
FIG. 9 shows a pyrolysis subsystem configured to pyrolyze residual biomass to hydrocarbons.

FIG. 9 depicts an exemplary pyrolysis subsystem that may be suitable for incorporating into an embodiment of the biomass conversion system. Raw biomass or residual biomass originating from one or more biomass conversion subsystems is collected and dried to an acceptable moisture content using dryer 910. Once dried, the biomass is typically processed (e.g. pulverized, micronized) to reduce the size of the residual biomass to a composition similar to sawdust. The processed residual biomass is then injected into a pyrolysis reactor 920 where the residual biomass is broken down in the absence of oxygen at about 500° C. to form pyrolysis gases and/or pyrolysis oils ("pyoil" or pyro-oil"). The pyrolysis gases typically comprise mixed hydrocarbons including alkanes and alkenes, such as ethane, ethylene, propane, propylene, with some residual decomposition gases, including amines and sulfides. Typically cyclone 930 is used to separate the hydrocarbon gasses from char. In some embodiments, pyrolysis gasses may be directly incorporated into the fuel conversion subsystem. In other embodiments, the pyrolysis gasses may be cooled in heat exchanger 940 to allow the separation 950 of pyrolysis oil and pyrolysis gasses. The oil or the gasses may be directly burned to provide thermal energy for one or more processes in the other subsystems. The pyrolysis oil comprises a mixture of long chain hydrocarbons, and oxygenated hydrocarbons which can be used as a fuel for one or more processes in the other subsystems. Pyrolysis reactors suitable to be used as subsystems for certain embodiments may be obtained from companies such as, but not limited to, Dynamotive Energy Systems (McLean, Va.).

In some cases it may be beneficial to separate the component parts of the hydrocarbon gasses in order to produce (relatively) pure components that can be used for other processes, or sold as a bulk chemical. Methods for separating gas mixtures are known to those of skill in the art, and may include, but need not be limited to, membrane filtration, absorption, and cryogenic separations. Gas separation equipment suitable for use with certain embodiments may be obtained from companies such as, but not limited to, Praxair, Inc. (Danbury, Conn.).

The gasification and pyrolysis systems depicted in FIGS. 8 & 9 are intended to be illustrative, and are not intended to limit the scope of the invention. Other methods of producing heat and process gasses from residual biomass are also known to those of skill in the art. For example, the residual biomass may be dried and pelletized for use directly in burners and or boilers to provide heat for various processes requiring the additional of thermal energy. Additionally, it is anticipated that new methods for producing heat and process gasses are likely to be discovered in the near future.

Figure 10:
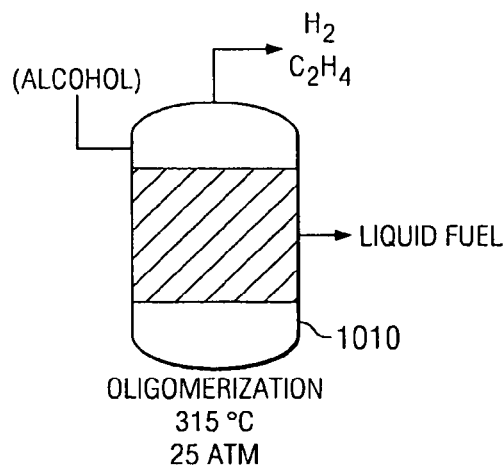
FIG. 10 shows a fuel conversion subsystem used to convert alcohol to a biofuel.

For embodiments comprising biomass conversion subsystems that produce primary or secondary alcohols, it is beneficial to directly convert the alcohols to longer chain hydrocarbons suitable as fuels. As shown in FIG. 10, alcohols may be directly oligomerized to hydrocarbons in at high temperatures (300-450° C.) and moderate pressures (1-40 atm) in the presence of a zeolite catalyst in an oligomerization reactor 1010. This conversion processes involves the dehydration of the alcohol to form an alkene (olefin), and the subsequent oligomerization of the alkenes to liquid hydrocarbons. By controlling the temperature and pressure of the oligomerization process and/or the composition of the zeolite, it is possible to direct the production of longer or shorter chain hydrocarbons. It is also possible to control the amount of alkane branching in the final product. The thermal energy required for the oligomerization process may be augmented with thermal energy taken from the gasification subsystem, and/or the reactor may be heated via the combustion of pyoil.

In some embodiments, oligomerization reactor 1010 may produce an amount of residual light hydrocarbons (lightends), e.g. short chain liquid and gaseous hydrocarbons. These light ends may be thermally reformed with steam to produce methanol and other primary alcohols which can be fed into the oliogmerization reactor in order to boost the fuel output. (See also FIG. 18). In other embodiments, the light ends may be recycled to create methanol and the methanol converted to long chain liquid hydrocarbons using the MOBIL methanol to fuel process.

For embodiments comprising biomass conversion subsystems that produce methane gas, it is beneficial to convert the methane to hydrocarbons suitable as fuels with a gas to fuel subsystem, such as the one depicted in FIG. 11. Briefly, the gas to fuel system in FIG. 11 comprises a four stage conversion process including a hydrocarbon to acetylene conversion process 1110, an absorption process 1120, a hydrogenation process 1130, and an oligomerization process 1140. Conversion process 1110 involves the conversion of methane to acetylene at very high temperatures (2000-2300° C.) in the presence of oxygen. The absorption process 1120 entails the absorption and purification of acetylene at high pressure (5-200 atm). The hydrogenation process 1130 involves the hydrogenation of acetylene to ethylene at moderate temperatures and high hydrogen pressures (5-150 atm). The oligomerization process 1140 entails the oligomerization of ethylene to normal alkanes and other branched hydrocarbons. Additional details of this gas to liquid conversion process can be found in U.S. Pat. Nos. 6,130,260, 6,323,247, 6,433,235, 6,602,920, 7,045,670, 7,119,240, 7,183,451, 7,208,647, and 7,250,449.

According to the methods and systems of certain embodiments, the thermal energy required for the conversion of methane to acetylene may be augmented with thermal energy taken from the gasification subsystem, and/or the conversion of methane to acetylene may be heated via the combustion of pyoil. When done in conjunction with gasification, the hydrogen needed for the hydrogenation step may be recovered from the syn gas. In other embodiments, it may be beneficial to use steam reformed biogas or landfill gasses to produce hydrogen for the hydrogenation step.

In some embodiments, in which both a stream of methane and a stream of alcohol are produced, it is possible to combine the alcohol oligomerization subsystem shown in FIG. 10 with the gas to fuels subsystem shown in FIG. 11. The combined system, shown in FIG. 12, has all of the components of the gas to fuel system shown in FIG. 11, e.g. a hydrocarbon to acetylene conversion process 1210, an absorption process 1220, a hydrogenation process 1230, and an oligomerization process

1240. However, the oligomerization process 1240 has the ability to simultaneously oligomerize alcohols to fuel, as is done in the oligomerization process 1010 shown in FIG. 10. Again, the fuel conversion subsystem of FIG. 12 may benefit from the integrated use of thermal energy and/or gases produced in gasification and or pyrolysis processes.

Figure 13:
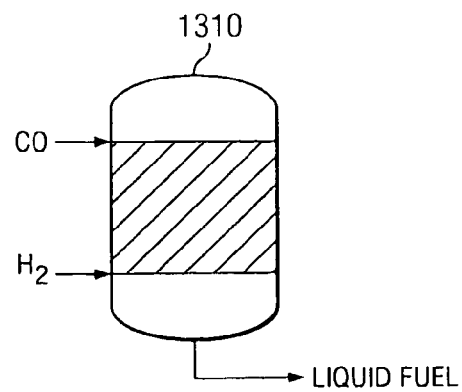
FIG. 13 shows a fuel conversion subsystem used to convert CO and hydrogen to a biofuel.

Embodiments comprising a gasification subsystem may optionally comprise a Fisher-Tropsch reactor 1310 that is independently capable of producing a mixture of normal alkanes and alkenes which are suitable for use as fuel. As shown in FIG. 13, a syn gas comprising CO and $H_2$ is reacted in the presence of iron or cobalt catalyst at a temperature range of approximately 200-300° C. Multiple Fisher-Tropsch reactor designs are known to those of skill in the art, such as multitubular fixed bed, slurry, and fluidized bed reactors. These reactor types are not individually depicted in FIG. 13, however one of skill in the art may reference any of a number of sources, such as Dry (Journal of Chemical Technology and Biotechnology, vol. 77, p. 43, 2001).

The fuel conversion subsystems depicted in FIGS. 10-13 are intended to be illustrative, and are not intended to limit the scope of the invention. Other methods of producing liquid hydrocarbon fuels from methane and/or alcohols are also known to those of skill in the art. For example, methane may be converted to methanol and ultimately to gasoline using the methanol activation technology developed by Mobil Corporation and commercialized in New Zealand. Additionally, it is anticipated that new methods of producing liquid hydrocarbon fuels from methane and/or alcohols are likely to be discovered in the near future.

Figure 1:
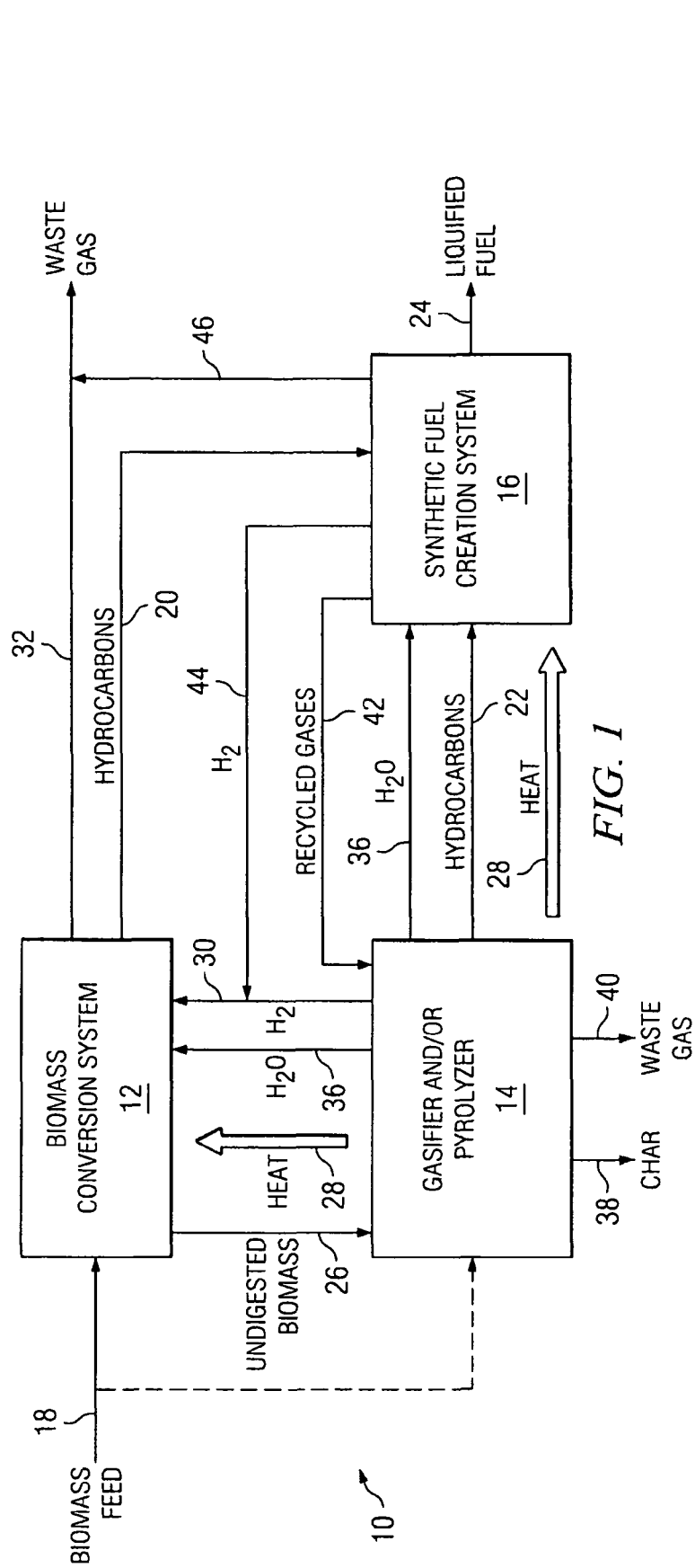
FIG. 1 is a diagram showing a generalized embodiment of a biofuel processing system according to the teachings of the present disclosure.

FIG. 1 shows a general embodiment of an integrated biofuel processing system 10 of an embodiment, including biomass conversion subsystem 12, gasification or pyrolysis reactor 14, and synthetic fuel creation subsystem 16, coupled as shown. Biomass conversion subsystem 12 receives biomass 18 to create methane and/or alcohol 20. Gasification or pyrolysis reactor 14 receives a residual biomass stream 26 from biomass conversion system 12 and converts residual biomass stream 26 to hydrocarbon gases, syn gas, and/or pyrolysis oil 22. The methane and/or alcohol 20 and hydrocarbon gases, syn gas, and/or pyrolysis oil 22 are fed to synthetic fuel creation system 16, which converts the methane and/or alcohol 20 and hydrocarbon gases, syn gas, and/or pyrolysis oil 22 to a liquid hydrocarbon fuel 24, such as gasoline or another generally high-molecular-weight fuel.

Biomass conversion system 12 receives any suitable form of organic matter, including, but not limited to, those shown in FIG. 4. As discussed above, biomass conversion system 12 may include many different subsystems, such as those shown in FIGS. 2A-2B and 5-7, for example. Biomass conversion system 12 may comprise any number of biological cultures that promote the decomposition of biomass 18 using a fermentation process for the production of alcohols, such as ethanol. In another embodiment, biomass conversion system 12 may include biological cultures that promote the decomposition of biomass feed 18 using a digester process for the production of methane. In another embodiment, biomass conversion system 12 may include a fermentation process and a digester process that coexist with one another. That is, a fermentation process and a digester process may be integrated within biomass conversion system 12 to generate alcohol and methane, respectively, that synthetic fuel creation system 16 uses to generate liquid hydrocarbon fuel 24.

Certain embodiments incorporating an integral fermentation and digester process may reduce the need to filter biomass feed 18 prior to processing by biomass conversion system 12. Particular types of biomass, such as grain sorghum or corn, may include glucose that is generally more conducive to decomposition using the fermentation process. Conversely, other types of biomass, such as those containing cellulose may be relatively more conducive to decomposition using a digester process. Selective separation or filtering of these types of biomass may not be required by biomass conversion system 12 due to its integral fermentation and digester process. In some embodiments therefore, biomass conversion system 12 may operate at a reduced cost relative to known biofuel processing systems, such as those described above.

Gasification or pyrolysis reactor 14 may generate heat 28, a hydrogen stream 30, a water stream 36, char 38, and waste gases 40 from residual biomass stream 26 by reacting residual biomass 26 at a relatively high temperature with a controlled amount of oxygen. In one embodiment, hydrogen stream 30 may be used to generate additional heat 28 for biomass conversion system 12 and/or synthetic fuel creation system 16. In another embodiment, hydrogen stream 30 may be transmitted to biomass conversion system 12 to produce alcohols from intermediate chemicals. In some embodiments, heat 28 may also include waste heat from the gasification process. Waste heat generally refers to excess thermal energy generated by gasification or pyrolysis reactor 14. This waste heat may be used for other processes, such as biomass conversion system 12 and/or synthetic fuel creation system 16.

In an embodiment in which gasification or pyrolysis reactor 14 includes a pyrolyzer reactor, the pyrolyzer that pyrolyzes the residual biomass stream 26 to form water stream 36 and hydrocarbon gases and/or pyrolysis oil 22. The pyrolyzer may reduce the relative amount of char 38, waste gas 40, or waste gas 32 produced by biofuel processing system 10. Waste from the reactor 14 may be emitted as char 38 and waste gas 40. The pyrolyzer is generally operable to convert most forms of biomass into streams that can be converted into useable energy. Pyrolyzer 14 may accept various forms of biomass similarly to biomass conversion system 12 as well as other nonbiodegradable components of biomass feed, such as plastics. Water stream 36 may be transferred to biomass conversion system 12 and/or synthetic fuel creation system 16. In some regions in which access to water may be scarce, water stream 36 may be diverted to other systems. The methane and/or alcohol 20 may be transferred to synthetic fuel creation system 16 for production of liquid hydrocarbon fuel 24. Principally, pyrolyzer 14 can convert the lignin content of the biomass into hydrocarbons, thus allowing synthetic fuel creation process 16 to ultimately convert the lignin content into liquid hydrocarbon fuel 24.

In principle, using biomass conversion system 12, the easy-to-digest portions of biomass feed 18 are processed first, leaving the hard-to-digest portions for reactor 14. Processing the biomass feed 18 to a high conversion rate by biomass conversion system 12 may require a relatively long residence time. For example, to achieve approximately 80 percent conversion of the biomass feed 18 in biomass conversion system 12 typically requires approximately 3 months, whereas 70 percent conversion may require approximately 2 months. Thus in one embodiment, biomass conversion system 12 may have a conversion rate of biomass feed 18 to methane and/or alcohol 20 that is less than 70 percent. Incorporation of the reactor 14 having a pyrolyzer for processing of residual biomass stream 26 may provide a relatively shorter residence time in biomass conversion system 12. Gasification or pyrolysis reactor 14 may also reduce the amount of residue in the form of waste gas 32, char 38, waste gas 40 generated by biofuel processing system 10 in some embodiments.

The product spectrum of gasification reactor 14 depends upon how it operates. If the oxygen to biomass ratio is high, the products favor carbon monoxide and hydrogen with less char 38. Unfortunately, because of the high oxygen usage, a greater portion of the biomass energy is lost as heat and relatively more cost may be associated with producing the oxygen. If the oxygen to biomass ratio is low, relatively more hydrocarbons and char may be formed. Thus, the oxygen to biomass ratio may be tailored to suit various types of operating conditions of biofuel processing system 10.

Fuel conversion subsystem 16 creates liquid hydrocarbon fuel 24, such as gasoline, jet fuel, and/or diesel and a waste gas stream 46 from methane and/or alcohol 20 and hydrocarbon gases, syn gas, and/or pyrolysis oil 22. In one embodiment, as described above as the gas to liquid method, synthetic fuel creation system 16 includes a relatively high temperature cracker that converts low-molecular-weight hydrocarbons, such as methane, into acetylene and hydrogen. After quenching, the acetylene and a portion of the hydrogen are converted catalytically into ethylene. The ethylene next passes over an oligomerization catalyst to produce liquid hydrocarbon fuel 24, which may be, for example, gasoline, jet fuel, diesel, or a fuel mix. The same catalyst may also convert alcohols from methane and/or alcohol 20 and hydrocarbon gases, syn gas, and/or pyrolysis oil 22 to liquid hydrocarbon fuel 24. Synthetic fuel creation system 16 may also generate a hydrogen stream 44 that may be fed to biomass conversion system 12. In one embodiment, synthetic fuel creation system 16 may also generate a recycle gas stream 42 that may be used by reactor 14.

Certain embodiments incorporating synthetic fuel creation system 16 may provide an advantage in that in the event that biomass feed 18 is not available because of storms, drought, disease, or an upset in the fermentation, synthetic fuel creation system 16 can process natural gas into fuels or chemicals until biomass conversion system 12 is again available.

Figure 14:
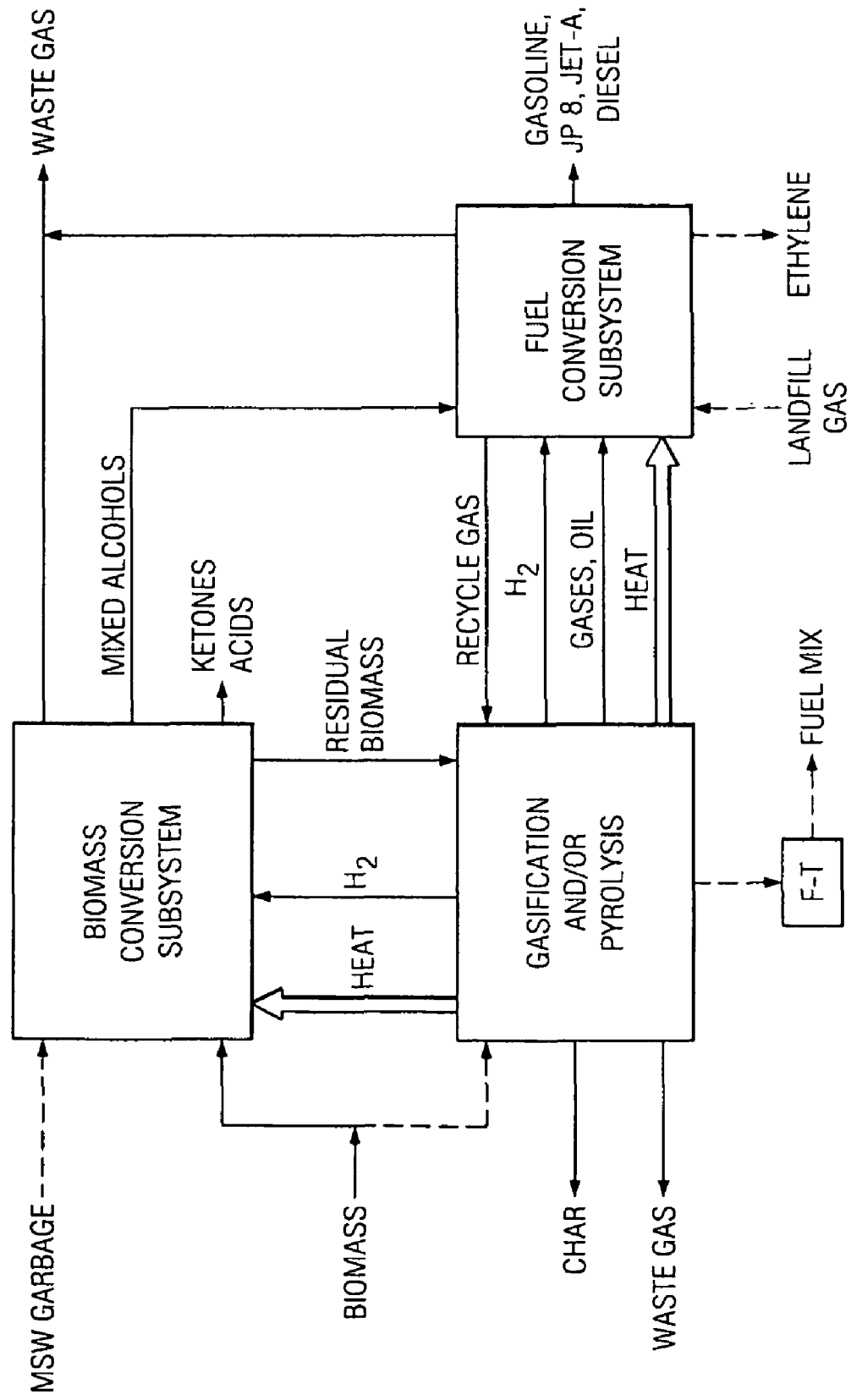
FIG. 14 depicts a generalized integrated biofuel production system according to an embodiment of the present disclosure.

FIG. 14 shows an additional general embodiment. The integrated biofuel production system shown in FIG. 14 also comprises a biomass conversion subsystem, a gasification/pyrolysis subsystem, and a fuel conversion subsystem. The various arrows represent the transfer of process gasses as well as heat. FIG. 14 also shows that various chemicals, such as ketones, carboxylic acids, and ethylene may be taken from the process stream. These bulk chemicals are valuable, however the demand for these chemicals fluctuates greatly depending upon consumption of end products for which these bulk chemicals are used. For example, a downturn in construction typically leads to diminished demand for ethylene. A wide variety of additional bulk chemicals may also be produced by the fuel conversion subsystem by varying the temperature, pressure, or catalyst of various processes in the fuel conversion subsystem.

EXAMPLES

Example 1

Conversion of Switchgrass to Gasoline using Fermentation to Carboxylate Salts, Pyrolysis, and Gas-to-Liquid Fuel Synthesis One hundred tonnes of switchgrass (comprising approximately 70% holocellulose and 30% lignin) is mixed with 15 tonnes of slaked lime ($Ca(OH)_2$)). After pretreatment is completed, it is allowed to ferment anaerobically in a lined pit with selected microorganisms and methanogen inhibitors for approximately 15 days at 55° C. in the presence of water and air. During the fermentation, the microbes selectively produce carboxylic acids which dissolve in the water and pass to the bottom of the pit where the dissolved acids are collected. The dissolved acids are neutralized with $CaCO_3$ as they are collected to produce an aqueous broth of carboxylic acid salts. After four weeks of fermentation, approximately 42 tonnes of $CaCO_3$ has been used to produce approximately 1000 tonnes of broth containing dissolved carboxylic acid salts. During the fermentation process, the 100 tonnes of biomass and 15 tonnes of lime are converted to 55 tonnes of wet residual biomass. The fermentation additionally produces approximately 37 tonnes of $CO_2$, which is captured for industrial processing.

The 1000 tonnes of broth is collected in a tank. The broth contains approximately 0.5% (by weight) aqueous acetic acid, propionic acid, and butric acid. As the broth settles, various undesired particulates are removed from the bottom of the tank and scum is removed from the top of the broth. Approximately 50 tonnes of mixed carboxylic acid salts are removed from the 1000 tonnes of cleaned broth via vapor-compression desalinization. The remaining water is recycled for use in later fermentation processes. The 50 tonnes of mixed carboxylic acid salts are converted to approximately 27 tonnes of mixed ketones and approximately 40 tonnes of calcium carbonate by pyrolytic conversion in a reduced atmosphere. The calcium carbonate is recycled for neutralizing additional dissolved acids. The 27 tonnes of mixed ketones are then converted to approximately 27 tonnes of secondary alcohols by hydrogenation over a nickel catalyst at approximately 130° C. and 15 tam $H_2$.

The 55 tonnes of wet residual biomass is then dried to reduce the moisture content, producing 35 tonnes of a slaked lime and dry residual biomass mixture. The slaked lime and dry residual contains approximately 20 tonnes of dry residual biomass, which is mostly lignin that was not digested during the fermentation process. After drying, the mixture of slaked lime and dry residual biomass is fed into a fluidized bed gasifier, operating at 1000° C., which converts the dry residual biomass into approximately 32 tonnes of CO, 10 tonnes of $N_2$ and 2 tonnes of $H_2$, in addition to small amounts $CO_2$, $H_2S$ and HCl. The gasification process also results in the formation of approximately 15.5 tonnes of char and ash by-product. The gasification products are cooled in a heat exchanger and then scrubbed to remove particulates, heavy metals, and unwanted gasses such as $H_2S$ and HCl. The $H_2$ is piped to the synthetic fuel facility where it is used for the hydrogenation of secondary alcohols converted into transportation fuels (below). The char and ash by-product of the gasification process is collected and sold as a soil additive. The residual CO is reacted with steam to produce hydrogen which is used for the hydrogenation steps of the alcohol to gasoline conversion process (below).

The 27 tonnes of secondary alcohols are oligomerized at 350° C. at 10 atm in the presence of zeolite catalysts and oxygen to produce 17 tonnes of gasoline (6,600 gal U.S.) and water.

Example 2

Conversion of Manure to Gasoline using Anaerobic Digester, gasification, and Gas-to-Liquid Fuel Synthesis One million, two hundred thousand liters of manure slurry from a 750-cow dairy farm are anaerobically digested by thermophilic methanogenic bacteria in a heated tank for approximately 15 days. During the course of the anaerobic digestion, approximately 1.6 $Mft^3$ of biogas is produced. As the biogas is produced, it is scrubbed to remove $H_2S$, and other contaminants, resulting in approximately 45,000 m³ (32 tonnes) of clean methane ($CH_4$) which is compressed for storage. After digestion, approximately one million liters of liquid fertilizer is recovered and sold for field application. After removal of the liquid component, approximately 120 tonnes of wet digested solids remain. The digested solids are dried to produce approximately 20 tonnes of dry residual biomass.

Twenty tonnes of dry residual biomass is mixed with approximately 15 tonnes of lime. The mixture of lime and dry residual biomass is fed into a fluidized bed gasifier, operating at 1000° C., which converts the dry residual biomass into approximately 32 tonnes of CO, 10 tonnes of $N_2$ and 2 tonnes of $H_2$, in addition to small amounts $CO_2$, $H_2S$ and HCl. The gasification process also results in the formation of approximately 15.5 tonnes of char and ash by-product. The gasification products are cooled in a heat exchanger and scrubbed to remove particulates, heavy metals, and unwanted gasses such as $H_2S$ and HCl. The CO and $H_2$ are piped to the synthetic fuel facility where they are converted into transportation fuels (below). The char and ash by-product of the gasification process is collected and sold as a soil additive.

The 32 tonnes of methane is fed into the thermal conversion stage of the gas-to-liquid fuel synthesis subsystem, along with 57 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 9 tonnes of gasoline (3,500 gal U.S.).

Example 3

Figure 15:
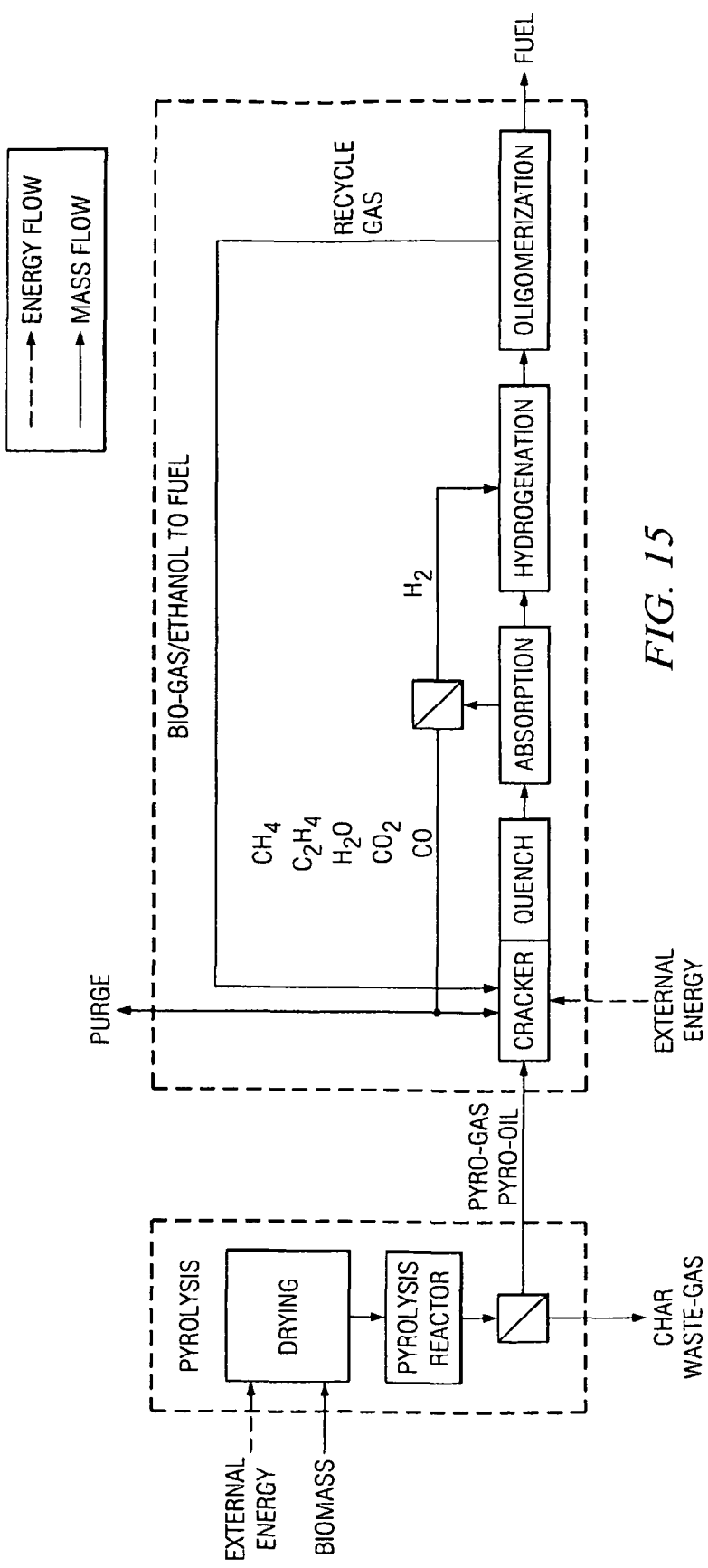
FIG. 15 shows an embodiment of an integrated biofuel processing system comprising pyrolysis and liquid hydrocarbon synthesis from mixed hydrocarbon gasses.

Conversion of Switchgrass to Liquid Hydrocarbon Fuel Using Pyrolysis and Gas-to-Liquid Fuel Synthesis FIG. 15 depicts the direct conversion of raw biomass to liquid hydrocarbon fuels using pyrolysis and a gas to liquid fuel conversion subsystem. One hundred tonnes of dried switchgrass is pulverized (micronized) resulting in 100 tonnes of dried, pulverized switchgrass with an average water content of 10%. The 100 tonnes of dried, pulverized switchgrass is fed into a pyrolysis reactor where the dried, pulverized switchgrass is flash pyrolyzed at approximately 500° C. to produce 76 tonnes of mixed hydrocarbon gasses and 14 tonnes of char. The char is separated from the hydrocarbon gasses and a small amount of vaporized pyrolysis oil with a cyclone, but the hot hydrocarbon gasses are not condensed to form pyrolysis oil.

The 76 tonnes of hot, mixed hydrocarbon gasses are fed into the thermal conversion stage of a gas-to-liquid fuel synthesis subsystem, along with 116 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 24 tonnes of liquid hydrocarbon fuel.

Example 4

Figure 16:
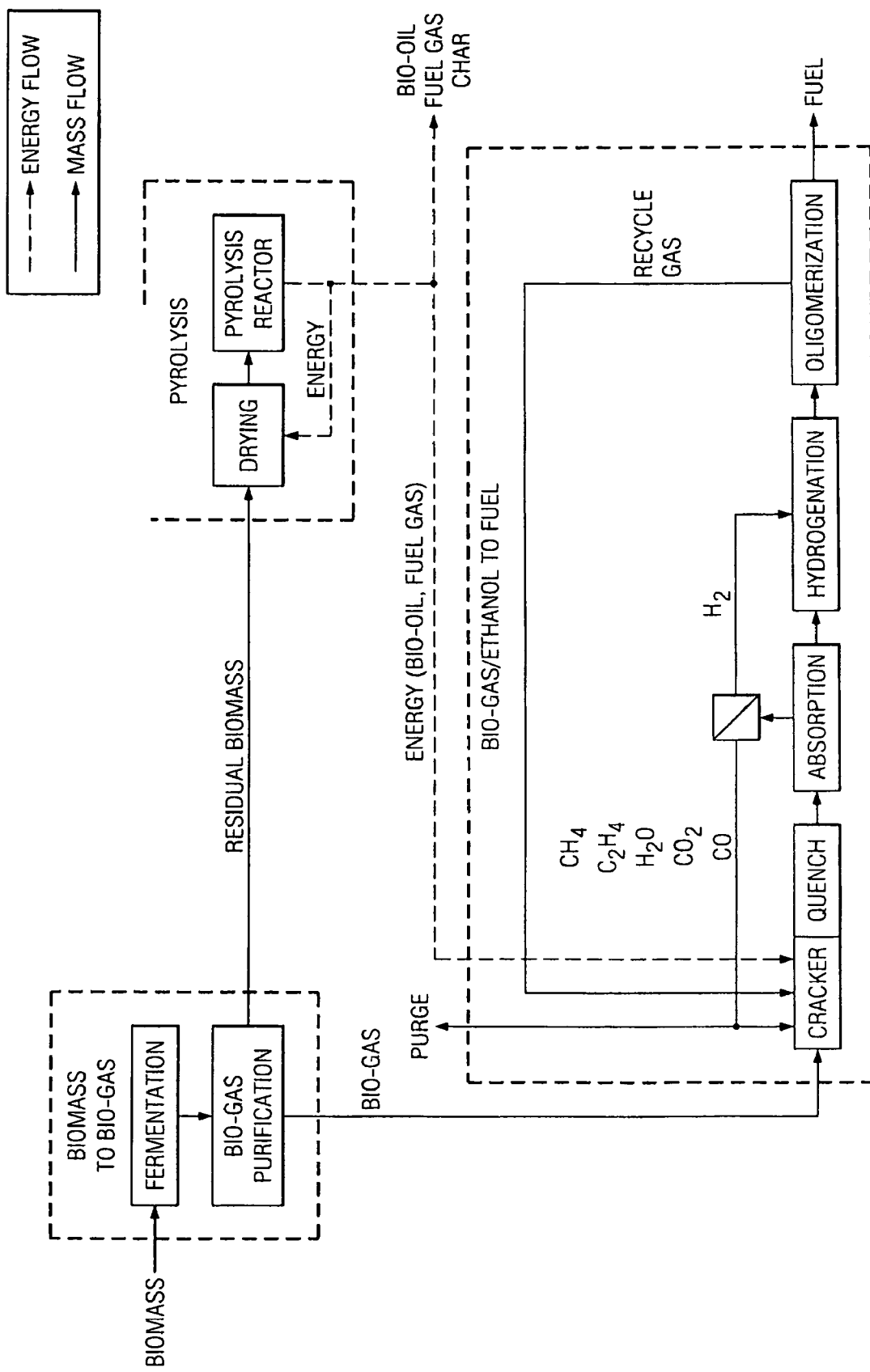
FIG. 16 shows an embodiment of an integrated biofuel processing system comprising anaerobic digestion, pyrolysis, and gasoline synthesis from methane.

Conversion of Municipal Solid Waste to Liquid Hydrocarbon Fuel Using Anaerobic Digestion, Pyrolysis, and Gas-to-Liquid Fuel Synthesis The biomass conversion system depicted in FIG. 16 is estimated to be able to produce approximately 7 tonnes of fuel from 63 tonnes of municipal solid waste. The mass and energy inputs and outputs for the individual subsystems are shown in FIG. 16. Sixty three tonnes of municipal solid waste (comprising 70% wt/wt holocellulose and 27% lignin) is mixed with 340 tonnes of water and 125 tonnes of inoculum (sludge) in an anaerobic digester and allowed to digest for approximately two weeks. During the digestion period, approximately 111 tonnes of biogas, comprising 80% carbon dioxide and 20% methane, is produced. Approximately 416 tonnes of wet residual biomass remains when the digestion is complete. The residual biomass is dried and pulverized in preparation for pyrolysis to produce 149 tonnes of dried, processed residual biomass. The biogas is purified to produce 23 tonnes of methane, which is fed into the gas-to-liquid fuel synthesis subsystem (below).

The 149 tonnes of dried residual biomass is fed into a pyrolysis reactor where the residual biomass is flash pyrolyzed at approximately 500° C. to produce 100 tonnes of pyrolysis oil, 18 tonnes of hydrocarbon gasses, and 20 tonnes of char. The 100 tonnes of pyrolysis oil can be used to provide heat for the drying of residual biomass or the thermal conversion of methane to acetylene in the gas-to-liquid fuel synthesis subsystem (below).

The 23 tonnes of methane is fed into the thermal conversion stage of the gas-to-liquid fuel synthesis subsystem, along with 41 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 7 tonnes of liquid hydrocarbon fuel.

The 18 tonnes of hydrocarbon gasses is also fed into the thermal conversion stage of the gas-to-liquid fuel synthesis subsystem, along with 29 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 5 additional tonnes of liquid hydrocarbon fuel.

The combustion of pyrolysis oil to produce energy for drying biomass and thermally converting methane to acetylene allows a dramatic reduction in the overall energy requirements for the biomass conversion. In particular the biomass conversion system depicted in FIG. 15 requires no external energy sources for the thermal conversion step of the gas-to-liquid fuel synthesis subsystem, which operates at nearly 2200° C. The electrical power needed to pump cooling/heating water and to convey materials can is provided by a wind turbine (not shown in FIG. 15) when the weather allows.

Example 5

Figure 18:
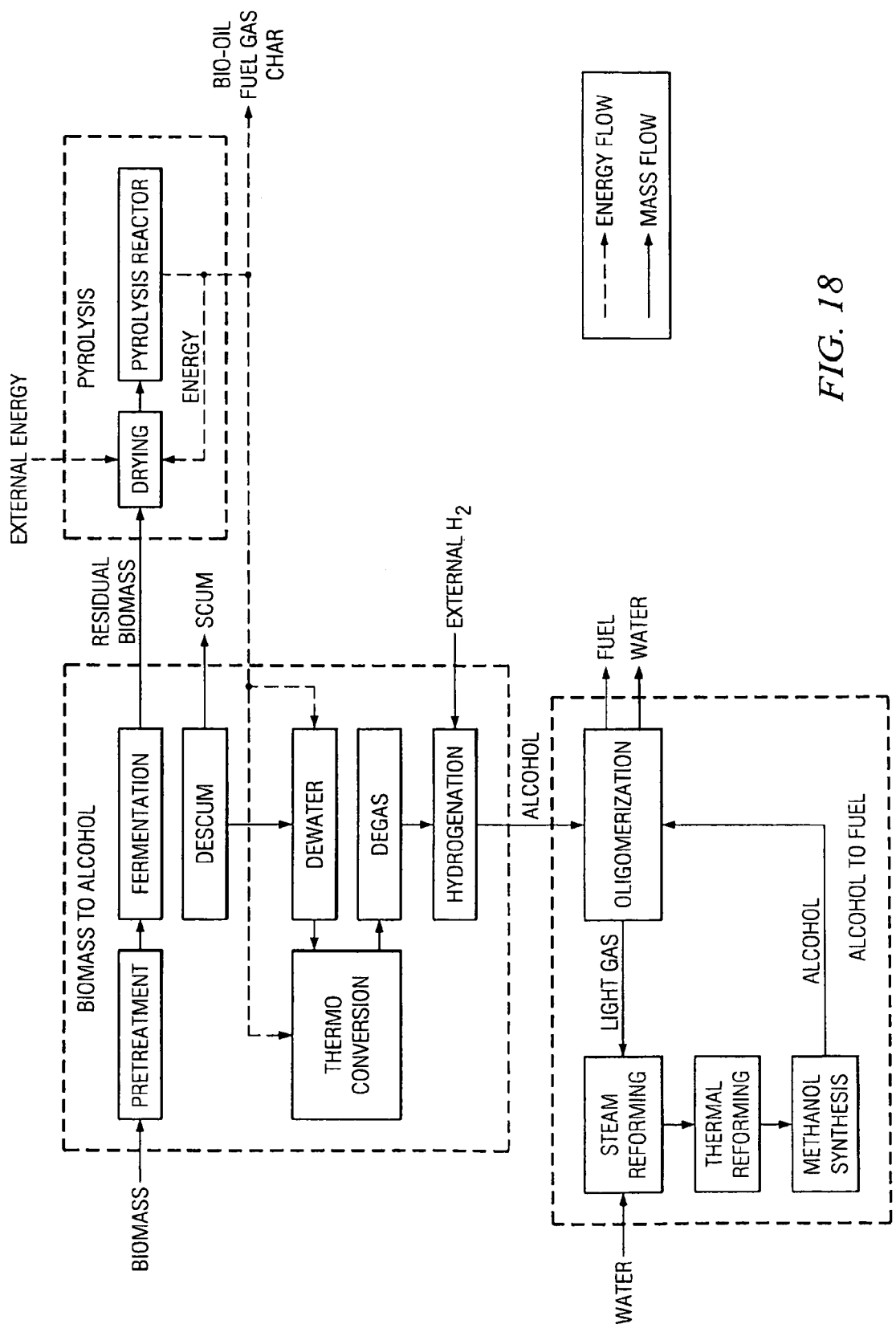
FIG. 18 shows another embodiment of an integrated biofuel processing system comprising anaerobic fermentation and production of alcohols, pyrolysis, and gasoline synthesis from alcohol.

Conversion of Switchgrass to Liquid Hydrocarbon Fuel Using Anaerobic Fermentation to Carboxylate Salts, Pyrolysis, and Oligomerization of Alcohol The biomass conversion system depicted in FIG. 18 is estimated to be able to produce approximately 17 tonnes of fuel from 100 tonnes of switchgrass. The mass and energy inputs and outputs for the individual subsystems are shown in FIG. 19. One hundred tonnes of switchgrass (comprising approximately 70% holocellulose and 27% lignin) is mixed with 15 tonnes of slaked lime ($Ca(OH)_2$)) and air. After the pretreatment is completed, 3 tonnes of inoculum (microorganisms and methanogen inhibitors) and allowed to ferment anaerobically in a lined pit for approximately four weeks at 55° C. in the presence of water. During the fermentation, approximately 984 tonnes of water and during pretreatment, 27 tonnes of air are added to the biomass. During the fermentation, the microbes selectively produce carboxylic acids which dissolve in the water and pass to the bottom of the pit where the dissolved acids are collected. The dissolved acids are neutralized with $CaCO_3$ as they are collected to produce an aqueous broth of carboxylic acid salts. After four weeks of fermentation, approximately 42 tonnes of $CaCO_3$ has been used to produce approximately 1000 tonnes of broth containing dissolved carboxylic acid salts. During the fermentation process, the 100 tonnes of biomass and 15 tonnes of slaked lime are converted to 61 tonnes of wet residual biomass. The fermentation additionally produces approximately 37 tonnes of $CO_2$, which is captured for industrial processing.

The 1000 tonnes of broth is collected in a tank. The broth contains approximately 0.5% (by weight) aqueous acetic acid, propionic acid, and butric acid. As the broth settles, various undesired particulates are removed from the bottom of the tank and scum is removed from the top of the broth. Approximately 50 tonnes of mixed carboxylic acid salts are removed from the 1000 tonnes of cleaned broth via vapor-compression desalinization. The remaining water is recycled for use in later fermentation processes. Approximately 27 tonnes of mixed ketones are drawn from the 50 tonnes of mixed carboxylic acid salts via thermal conversion and evaporative separation. The calcium carbonate residue is recycled for neutralizing additional dissolved acids. The 27 tonnes of mixed ketones are then converted to approximately 28 tonnes of secondary alcohols by hydrogenation over a nickel catalyst at approximately 130° C. and 15 atm $H_2$.

The 61 tonnes of wet residual biomass is dried to reduce the water content and pulverized to facilitate pyrolysis to produce 45 tonnes of dried, processed residual biomass. The 45 tonnes of dried, processed residual biomass is fed into a pyrolysis reactor where the dried, processed residual biomass is flash pyrolyzed at approximately 500° C. to produce 29 tonnes of pyrolysis oil, 5 tonnes of hydrocarbon gasses, and 6 tonnes of char. The 29 tonnes of pyrolysis oil is used to provide heat for the drying of wet residual biomass and the thermal conversion and evaporative separation of mixed ketones (above) and the oligomerization of secondary alcohols (below).

The 28 tonnes of secondary alcohols are oligomerized at 350° C. at 10 atm in the presence of zeolite catalysts to produce 12 tonnes of gasoline (6,600 gal U.S.), 5 tonnes of light hydrocarbon residuals and 20 tonnes of water. The 5 tonnes of light hydrocarbon residuals are steam- and thermally-reformed to produce 8 tonnes of methanol. The 8 tonnes of methanol is recycled to oligomerization reactor to produce an additional 5 tonnes of gasoline.

The combustion of pyrolysis oil to produce energy for drying biomass, thermally converting carboxylate salts to ketones, and oligomerizing secondary alcohols to fuel allows a dramatic reduction in the overall energy requirements for the biomass conversion. The electrical power needed to pump cooling/heating water and to convey materials is provided by a wind turbine (not shown in FIG. 18) when weather conditions allow.

Example 6

Figure 20:
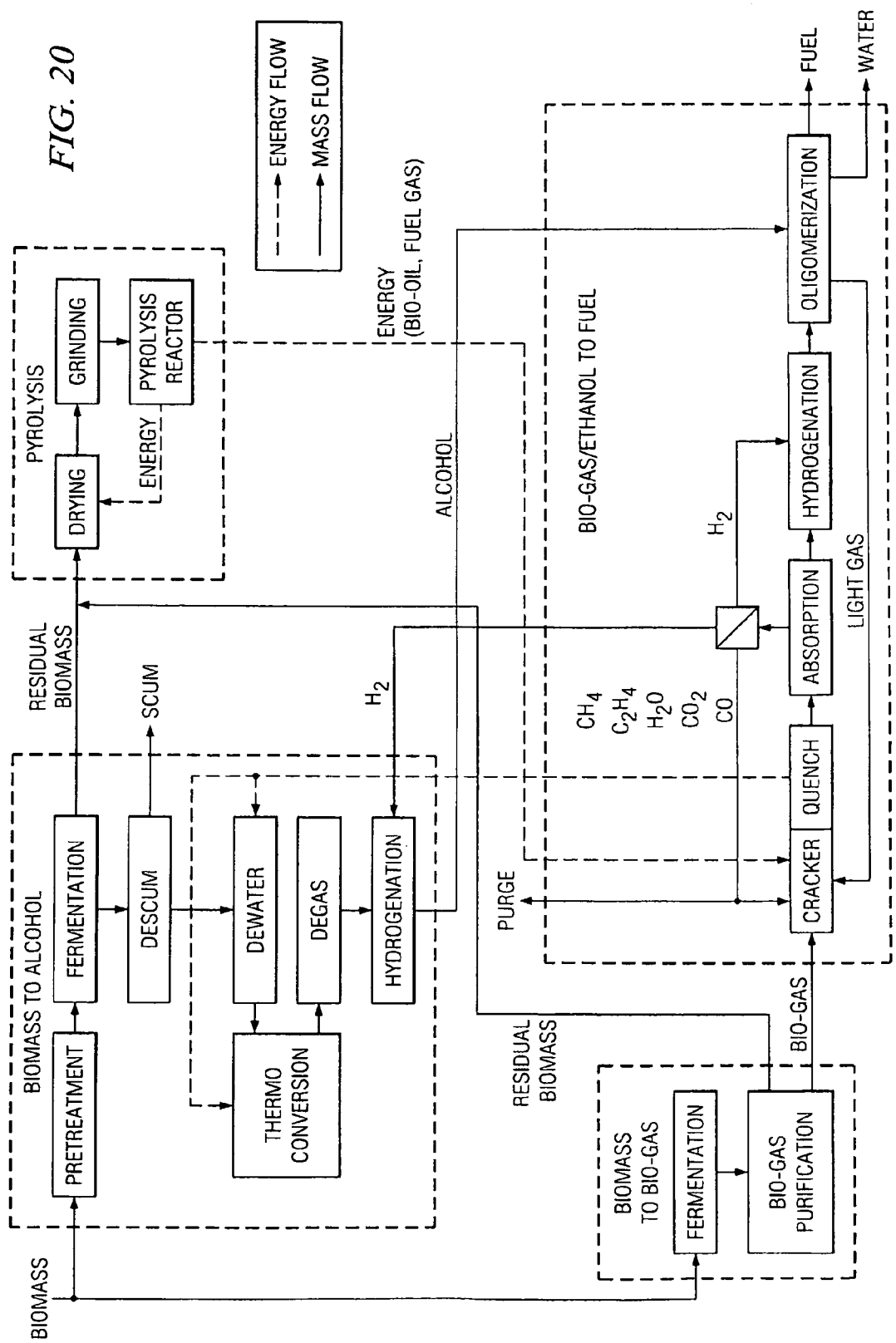
FIG. 20 shows another embodiment of an integrated biofuel processing system comprising anaerobic digestion, anaerobic fermentation and production of alcohols, pyrolysis, and gasoline synthesis from methane and alcohol.

Conversion of Switchgrass to Liquid Hydrocarbon Fuel Using Anaerobic Digestion, Anaerobic Fermentation to Carboxylate Salts, Pyrolysis, Gas-to-Liquid Fuel Synthesis, and Oligomerization of Alcohol The biomass conversion system depicted in FIG. 20 is estimated to be able to produce approximately 32 tonnes of fuel from 100 tonnes of switchgrass and 63 tonnes of municipal solid waste. The mass and energy inputs and outputs for the individual subsystems are shown in FIG. 20. One hundred tonnes of switchgrass (comprising approximately 70% holocellulose and 27% lignin) is mixed with 15 tonnes of slaked lime ($Ca(OH)_2$)). After the fermentation is completed, 3 tonnes of inoculum (microorganisms and methanogen inhibitors) and allowed to ferment anaerobically in a lined pit for approximately four weeks at 55° C. in the presence of water and air. During the fermentation, approximately 992 tonnes of water and during the pretreatment, 27 tonnes of air are added to the biomass. During the fermentation, the microbes selectively produce carboxylic acids which dissolve in the water and pass to the bottom of the pit where the dissolved acids are collected. The dissolved acids are neutralized with $CaCO_3$ as they are collected to produce an aqueous broth of carboxylic acid salts. After four weeks of fermentation, approximately 42 tonnes of $CaCO_3$ has been used to produce approximately 1000 tonnes of broth containing dissolved carboxylic acid salts. During the fermentation process, the 100 tonnes of biomass and 15 tonnes of slaked lime are converted to 61 tonnes of wet residual biomass. The fermentation additionally produces approximately 37 tonnes of $CO_2$, which is captured for industrial processing.

The 1000 tonnes of broth is collected in a tank. The broth contains approximately 0.5% (by weight) aqueous acetic acid, propionic acid, and butric acid. As the broth settles, various undesired particulates are removed from the bottom of the tank and scum is removed from the top of the broth. Approximately 50 tonnes of mixed carboxylic acid salts are removed from the 1000 tonnes of cleaned broth via vapor-compression desalinization. The remaining water is recycled for use in later fermentation processes. Approximately 27 tonnes of mixed ketones are drawn from the 50 tonnes of mixed carboxylic acid salts via thermal conversion and evaporative separation. The calcium carbonate residue is recycled for neutralizing additional dissolved acids. The 27 tonnes of mixed ketones are then converted to approximately 28 tonnes of secondary alcohols by hydrogenation over a nickel catalyst at approximately 130° C. and 15 atm $H_2$.

Concurrently with the fermentation of switchgrass, 63 tonnes of municipal solid waste (comprising 70% wt/wt holocellulose and 27%) is mixed with 340 tonnes of water and 125 tonnes of inoculum (sludge) in an anaerobic digester and allowed to digest for approximately two weeks. During the digestion period, approximately 111 tonnes of biogas, comprising 80% carbon dioxide and 20% methane, is produced. Approximately 416 tonnes of residual biomass remains when the digestion is complete. The residual biomass is dried and pulverized in preparation for pyrolysis to produce 149 tonnes of dried, pulverized residual biomass. The biogas is purified to produce 23 tonnes of methane, which is fed into the gas-to-liquid fuel synthesis subsystem (below).

The dried, pulverized residual biomass from the fermentation of switchgrass and the anaerobic digestion of municipal solid waste is combined, resulting in 210 tonnes of dried, pulverized residual biomass. The 210 tonnes of dried, processed residual biomass is fed into a pyrolysis reactor where the dried, processed residual biomass is flash pyrolyzed at approximately 500° C. to produce 141 tonnes of pyrolysis oil, 25 tonnes of hydrocarbon gasses, and 28 tonnes of char. The 141 tonnes of pyrolysis oil is used to provide heat for the drying of wet residual biomass, the thermal conversion and evaporative separation of mixed ketones (above), the oligomerization of secondary alcohols (below), and the conversion of methane to acetylene (below).

The 28 tonnes of secondary alcohols are oligomerized at 350° C. at 10 atm in the presence of zeolite catalysts and oxygen to produce 17 tonnes of gasoline (6,600 gal U.S.) and 11 tonnes of water.

The 23 tonnes of methane is fed into the thermal conversion stage of the gas-to-liquid fuel synthesis subsystem, along with 41 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 7 tonnes of liquid hydrocarbon fuel.

The 25 tonnes of hydrocarbon gasses is also fed into the thermal conversion stage of the gas-to-liquid fuel synthesis subsystem, along with 44 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 8 additional tonnes of liquid hydrocarbon fuel.

The combustion of pyrolysis oil to produce energy for drying biomass, thermally converting carboxylate salts to ketones, converting methane and hydrocarbon gasses to acetylene, and oligomerizing secondary alcohols to fuel allows a dramatic reduction in the overall energy requirements for the biomass conversion. The electrical power needed to pump cooling/heating water and to convey materials is provided by a wind turbine (not shown in FIG. 18) when weather conditions allow.

Example 7

Figure 22:
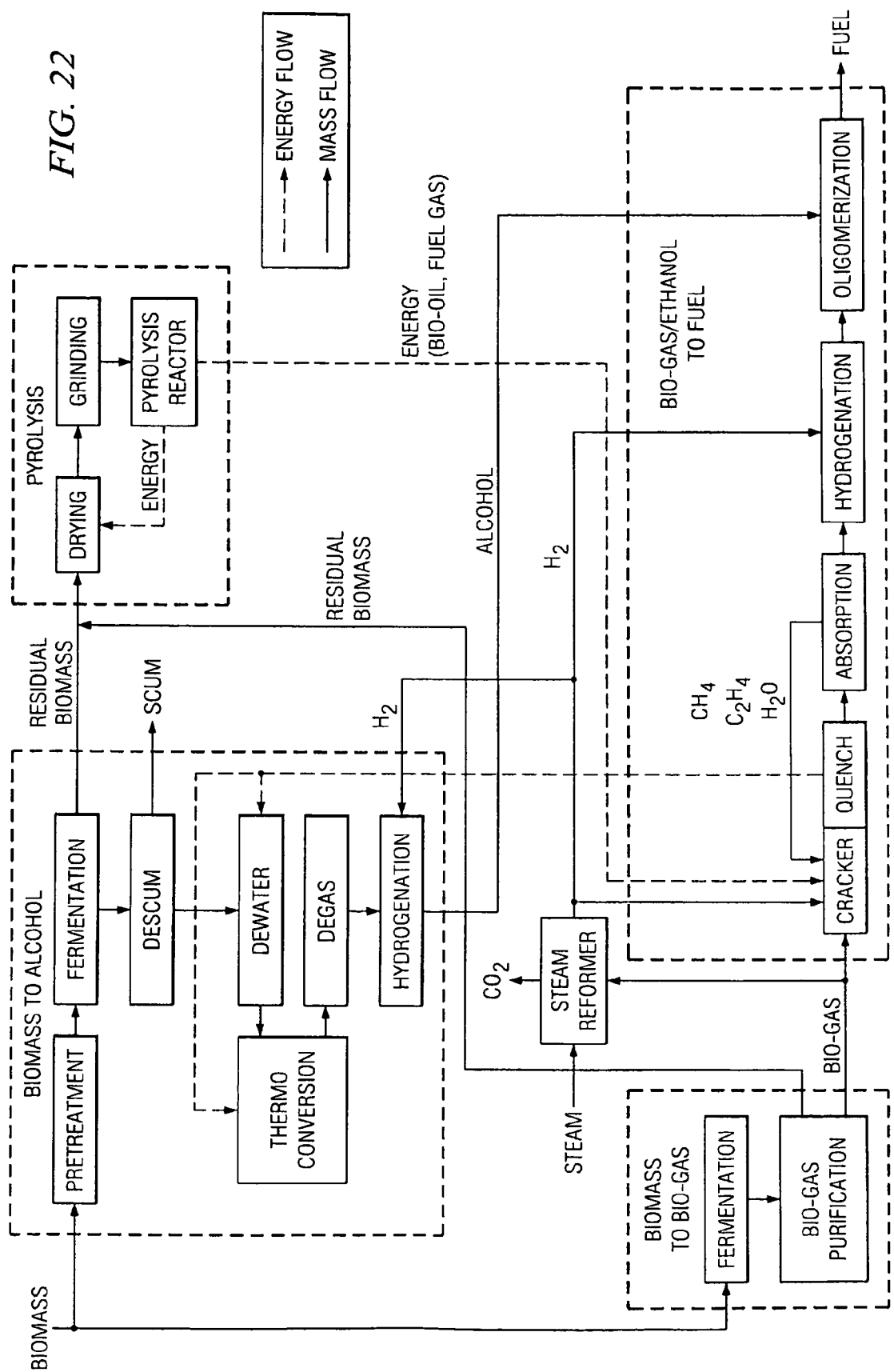
FIG. 22 shows another embodiment of an integrated biofuel processing system comprising anaerobic digestion, anaerobic fermentation and production of alcohols, pyrolysis, and gasoline synthesis from methane and alcohol with additional steam reforming of bio-gas to produce hydrogen gas for hydrogenation.

Conversion of Switchgrass to Liquid Hydrocarbon Fuel Using Anaerobic Digestion, Steam Reforming of Methane, Anaerobic Fermentation to Carboxylate Salts, Pyrolysis, Gas-to-Liquid Fuel Synthesis, and Oligomerization of Alcohol The biomass conversion system depicted in FIG. 22 is estimated to be able to produce approximately 30 tonnes of fuel from 100 tonnes of switchgrass and 63 tonnes of municipal solid waste. One hundred tonnes of switchgrass (comprising approximately 70% holocellulose and 27% lignin) is mixed with 15 tonnes of slaked lime ($Ca(OH)_2$)). After pretreatment is completed, 3 tonnes of inoculum (microorganisms and methanogen inhibitors) and allowed to ferment anaerobically in a lined pit for approximately four weeks at 55° C. in the presence of water and air. During the fermentation, approximately 992 tonnes of water and during pretreatment, 27 tonnes of air are added to the biomass. During the fermentation, the microbes selectively produce carboxylic acids which dissolve in the water and pass to the bottom of the pit where the dissolved acids are collected. The dissolved acids are neutralized with $CaCO_3$ as they are collected to produce an aqueous broth of carboxylic acid salts. After four weeks of fermentation, approximately 42 tonnes of $CaCO_3$ has been used to produce approximately 1000 tonnes of broth containing dissolved carboxylic acid salts. During the fermentation process, the 100 tonnes of biomass and 15 tonnes of slaked lime are converted to 61 tonnes of wet residual biomass. The fermentation additionally produces approximately 37 tonnes of $CO_2$, which is captured for industrial processing.

The 1000 tonnes of broth is collected in a tank. The broth contains approximately 0.5% (by weight) aqueous acetic acid, propionic acid, and butric acid. As the broth settles, various undesired particulates are removed from the bottom of the tank and scum is removed from the top of the broth. Approximately 50 tonnes of mixed carboxylic acid salts are removed from the 1000 tonnes of cleaned broth via vapor-compression desalinization. The remaining water is recycled for use in later fermentation processes. Approximately 27 tonnes of mixed ketones are drawn from the 50 tonnes of mixed carboxylic acid salts via thermal conversion and evaporative separation. The calcium carbonate residue is recycled for neutralizing additional dissolved acids. The 27 tonnes of mixed ketones are then converted to approximately 28 tonnes of secondary alcohols by hydrogenation over a nickel catalyst at approximately 130° C. and 15 atm $H_2$.

Concurrently with the fermentation of switchgrass, 63 tonnes of municipal solid waste (comprising 70% wt/wt holocellulose and 27%) is mixed with 340 tonnes of water and 125 tonnes of inoculum (sludge) in an anaerobic digester and allowed to digest for approximately two weeks. During the digestion period, approximately 111 tonnes of biogas, comprising 80% carbon dioxide and 20% methane, is produced. Approximately 416 tonnes of residual biomass remains when the digestion is complete. The residual biomass is dried and pulverized in preparation for pyrolysis to produce 149 tonnes of dried, pulverized residual biomass. The biogas is purified to produce 23 tonnes of methane, which is fed into the gas-to-liquid fuel synthesis subsystem (below).

The dried, pulverized residual biomass from the fermentation of switchgrass and the anaerobic digestion of municipal solid waste is combined, resulting in 210 tonnes of dried, pulverized residual biomass. The 210 tonnes of dried, processed residual biomass is fed into a pyrolysis reactor where the dried, processed residual biomass is flash pyrolyzed at approximately 500° C. to produce 141 tonnes of pyrolysis oil, 25 tonnes of hydrocarbon gasses, and 28 tonnes of char. The 141 tonnes of pyrolysis oil is used to provide heat for the drying of wet residual biomass, the thermal conversion and evaporative separation of mixed ketones (above), the oligomerization of secondary alcohols (below), and the conversion of methane to acetylene (below).

The 28 tonnes of secondary alcohols are oligomerized at 350° C. at 10 atm in the presence of zeolite catalysts and oxygen to produce 17 tonnes of gasoline (6,600 gal U.S.) and 11 tonnes of water.

Twenty tones of the biogas are steam reformed to produce additional carbon dioxide and hydrogen. The hydrogen is filtered and used as a process gas for the hydrogenation of ketones, and the hydrogenation of acetylene to ethylene.

The remaining 91 tonnes of biogas is fed into the thermal conversion stage of the gas-to-liquid fuel synthesis subsystem, along with 41 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 5 tonnes of liquid hydrocarbon fuel.

The 25 tonnes of hydrocarbon gasses is also fed into the thermal conversion stage of the gas-to-liquid fuel synthesis subsystem, along with 44 tonnes of oxygen to produce a mixture of acetylene, methane, water, carbon dioxide, and carbon monoxide. The acetylene is purified, and the methane and carbon monoxide are separated for use in other processes. The acetylene is then hydrogenated to produce ethylene, which is oligomerized to produce approximately 8 additional tonnes of liquid hydrocarbon fuel.

The combustion of pyrolysis oil to produce energy for drying biomass, thermally converting carboxylate salts to ketones, converting methane and hydrocarbon gasses to acetylene, and oligomerizing secondary alcohols to fuel allows a dramatic reduction in the overall energy requirements for the biomass conversion. The electrical power needed to pump cooling/heating water and to convey materials is provided by a wind turbine (not shown in FIG. 18) when weather conditions allow.

Thus, certain embodiments provide for an integrated biomass conversion system that realizes efficiency gains from the production of valuable matter and energy streams from materials that might otherwise be discarded as waste. Using the systems of certain embodiments in conjunction with a source of renewable electrical energy, it is possible to produce "conventional" liquid hydrocarbon fuels from renewable feedstocks without the need for external petroleum based energy, such as natural gas or electricity from coal-fired power plants.

Although the present disclosure has been described with several embodiments, a myriad of changes, variations, alterations, transformations, and modifications may be suggested to one skilled in the art, and it is intended that the present disclosure encompass such changes, variations, alterations, transformation, and modifications as they fall within the scope of the appended claims.

The invention claimed is:

1. A biofuel production process comprising:
 a) converting biomass to alcohol, methane, or mixtures thereof and residual biomass;
 b) pyrolyzing the residual biomass to produce hydrocarbon gasses and or pyrolysis oil;
 c) synthesizing a liquid hydrocarbon fuel from the alcohol, methane or mixture thereof using some of the hydrocarbon gasses or pyrolysis oil produced by pyrolyzing the residual biomass, wherein step c) comprises oligomerizing the alcohol to form a liquid hydrocarbon fuel.

2. The process of claim 1, wherein step a) comprises:
 1) fermenting biomass to produce carboxylic acids or carboxylic acid salts;
 2) thermally converting the carboxylic acids or carboxylic acid salts to ketones; and
 3) hydrogenating the ketones to produce secondary alcohols.

3. The process of claim 2, wherein pyrolysis oil is combusted to produce heat to drive step a) 2).

4. The process of claim 2, further comprising pyrolyzing additional biomass in addition to the residual biomass to produce additional pyrolysis oil, and combusting the additional pyrolysis oil to drive step a) 2).

5. The process of claim 2, further comprising:
 f) converting a second biomass to methane and a second residual biomass or converting landfill gas to methane;
 g) reforming the methane to produce hydrogen;
 h) using the hydrogen to drive step a) 3).

6. The process of claim 1, wherein the biomass is converted to alcohol with enzymes.

7. The process of claim 1, wherein the biomass is converted to alcohol by microorganisms.

8. The process of claim 1, wherein the biomass is converted to methane by methanogenic bacteria.

9. The process of claim 1, wherein the biomass is selected from the group consisting of grasses, trees, canes, animal waste, food waste, algae, municipal solid waste, and harvest residuals.

10. The process of claim 1, wherein step c) comprises the steps of:
 1) thermally converting the methane to acetylene and residual gasses;
 2) separating the acetylene from the residual gases;
 3) hydrogenating the acetylene to form ethylene;
 4) oligomerizing the ethylene to form a hydrocarbon fuel.

11. The process of claim 10, further comprising pyrolyzing a second biomass to produce additional pyrolysis oil, and combusting the additional pyrolysis oil to produce heat to drive step c) 1).

12. The process of claim 10, further comprising recovering supplemental methane from landfill gas, and adding the supplemental methane to the methane for thermal conversion to acetylene and residual gases in step c) 1).

13. The process of claim 10, wherein pyrolysis oil is combusted to produce heat to drive step c) 1).

14. The process of claim 10, wherein:
 production of hydrocarbon gasses in step b) further includes $CO$, $H_2$, and $CO_2$; and
 the hydrocarbon gases, $CO$, $H_2$, and $CO_2$ are also converted to acetylene and residual gases in step c) 1).

15. The biofuel production process of claim 10, further comprising:
 f) converting a second biomass to supplemental methane and a second residual biomass or converting landfill gas to supplemental methane;
 g) steam reforming the supplemental methane to produce hydrogen;
 h) using the hydrogen to drive step c) 3).

16. The process of claim 1, wherein oligomerizing the alcohol additionally forms light hydrocarbon residuals and the light hydrocarbon residuals are converted to additional heavy hydrocarbons.

17. The process of claim 1, wherein the alcohol is oligomerized in the presence of a zeolite catalyst.

18. A biofuel production process comprising:
 a) converting biomass to alcohol, methane, or mixtures thereof and residual biomass;
 b) gasifying the residual biomass to produce carbon monoxide, hydrogen, or mixtures thereof, thereby producing thermal energy;
 c) synthesizing a liquid hydrocarbon fuel from the alcohol, methane or mixture thereof using some of the thermal energy produced by gasifying the residual biomass, wherein step c) comprises oligomerizing the alcohol to form a liquid hydrocarbon fuel.

19. The process of claim 18, wherein step a) uses some of the thermal energy produced by gasifying the residual biomass.

20. The process of claim 18, wherein step a) comprises:
 1) fermenting biomass to produce carboxylic acids or carboxylic acid salts;
 2) thermally converting the carboxylic acids or carboxylic acid salts to ketones; and
 3) hydrogenating the ketones to produce secondary alcohols.

21. The process of claim 20, further comprising pyrolyzing a second biomass to produce pyrolysis oil, and combusting the pyrolysis oil to drive step a) 2).

22. The process of claim 20, further comprising:
 f) converting a second biomass to methane and a second residual biomass or converting landfill gas to methane;
 g) reforming the methane to produce hydrogen;
 h) using the hydrogen to drive step a) 3).

23. The process of claim 18, wherein the biomass is converted to alcohol with enzymes.

24. The process of claim 18, wherein the biomass is converted to alcohol by microorganisms.

25. The process of claim 18, wherein the biomass is converted to methane by methanogenic bacteria.

26. The process of claim 18, wherein the biomass is selected from the group consisting of grasses, trees, canes, animal waste, food waste, algae, municipal solid waste, and harvest residuals.

27. The process of claim 18, wherein step c) comprises the steps of:
1) thermally converting the methane to acetylene and residual gases;
2) separating the acetylene from the residual gases;
3) hydrogenating the acetylene to form ethylene;
4) oligomerizing the ethylene to form a hydrocarbon fuel.

28. The biofuel production process of claim 27, further comprising:
f) converting a second biomass to supplemental methane and a second residual biomass or converting landfill gas to supplemental methane;
g) steam reforming the supplemental methane to produce hydrogen;
h) using the hydrogen to drive step c) 3).

29. The process of claim 27, further comprising recovering supplemental methane from landfill gas, and adding the supplemental methane to the methane for thermal conversion to acetylene and residual gases in step c) 1).

30. The process of claim 27, further comprising pyrolyzing a second biomass to produce pyrolysis oil, and combusting the pyrolysis oil to produce heat to drive step c) 1).

31. The process of claim 18, wherein oligomerizing the alcohol additionally forms light hydrocarbon residuals and the light hydrocarbon residuals are converted to additional alcohol.

32. The process of claim 18, wherein step c) comprises synthesizing a liquid hydrocarbon fuel from the carbon monoxide and the hydrogen using a Fisher-Tropsch reactor.

33. The process of claim 18, further comprising pyrolyzing the residual biomass to produce hydrocarbon gasses, CO, $H_2$, and $CO_2$ or pyrolysis oil.

34. The process of claim 18, wherein the alcohol is oligomerized in the presence of a zeolite catalyst.

35. A biofuel production process comprising:
a) pyrolyzing biomass to produce hydrocarbon gasses or pyrolysis oil;
b) synthesizing a liquid hydrocarbon fuel from the hydrocarbon gasses or pyrolysis oil, wherein step b) comprises the steps of:
1) thermally converting the hydrocarbon gasses or pyrolysis oil to acetylene and residual gases;
2) separating the acetylene from the residual gases;
3) hydrogenating the acetylene to form ethylene;
4) oligomerizing the ethylene to form a hydrocarbon fuel,
f) converting a second biomass to methane and a residual biomass or recovering methane from landfill gas;
g) steam reforming the methane to produce hydrogen;
h) using the hydrogen to drive step b) 3).

36. The process of claim 35, wherein prior to step a) the biomass is dried and micronized.

37. The process of claim 35, further comprising recovering methane from landfill gas, and adding the methane to the hydrocarbon gasses or pyrolysis oil for thermal conversion to acetylene and residual gases in step b) 1).

38. The process of claim 35, wherein pyrolysis oil is combusted to produce heat to drive step b) 1).

39. The process of claim 35, wherein the biomass is selected from the group consisting of grasses, trees, canes, animal waste, food waste, algae, municipal solid waste, and harvest residuals.

40. A biofuel production process comprising:
a) converting biomass to carboxylic acid salts and residual biomass;
b) converting the carboxylic acid salts to secondary alcohols;
c) gasifying the residual biomass to produce carbon monoxide and hydrogen, wherein the hydrogen is used to convert the carboxylic acid salts to secondary alcohols;
d) synthesizing a liquid hydrocarbon fuel from the secondary alcohols, wherein step d) comprises oligomerizing the alcohol to form a hydrocarbon fuel.

41. The biofuel production process of claim 40, wherein the alcohol is oligomerized in the presence of a zeolite catalyst.

42. A biofuel production process comprising:
a) converting biomass to alcohol, methane, or mixtures thereof and residual biomass, wherein step a) comprises:
1) fermenting biomass to produce carboxylic acids or carboxylic acid salts;
2) thermally converting the carboxylic acids or carboxylic acid salts to ketones; and
3) hydrogenating the ketones to produce secondary alcohols;
b) pyrolyzing the residual biomass to produce hydrocarbon gasses and or pyrolysis oil;
c) synthesizing a liquid hydrocarbon fuel from the alcohol, methane or mixture thereof using some of the hydrocarbon gasses or pyrolysis oil produced by pyrolyzing the residual biomass;
f) converting a second biomass to methane and a second residual biomass or converting landfill gas to methane;
g) reforming the methane to produce hydrogen;
h) using the hydrogen to drive step a) 3).

43. The process of claim 42, wherein pyrolysis oil is combusted to produce heat to drive step a) 2).

44. The process of claim 42, further comprising pyrolyzing additional biomass to produce additional pyrolysis oil, and combusting the additional pyrolysis oil to drive step a) 2).

45. A biofuel production process comprising:
a) converting biomass to alcohol, methane, or mixtures thereof and residual biomass;
b) pyrolyzing the residual biomass to produce hydrocarbon gasses and or pyrolysis oil;
c) synthesizing a liquid hydrocarbon fuel from the alcohol, methane or mixture thereof using some of the hydrocarbon gasses or pyrolysis oil produced by pyrolyzing the residual biomass, wherein step c) comprises the steps of:
1) thermally converting the methane to acetylene and residual gasses;
2) separating the acetylene from the residual gases;
3) hydrogenating the acetylene to form ethylene;
4) oligomerizing the ethylene to form a hydrocarbon fuel;
f) converting a second biomass to supplemental methane and a second residual biomass or converting landfill gas to supplemental methane;
g) steam reforming the supplemental methane to produce hydrogen;
h) using the hydrogen to drive step c) 3).

46. The process of claim 45, further comprising pyrolyzing a second biomass to produce additional pyrolysis oil, and combusting the additional pyrolysis oil to produce heat to drive step c) 1).

47. The process of claim 45, further comprising recovering supplemental methane from landfill gas, and adding the supplemental methane to the methane for thermal conversion to acetylene and residual gases in step c) 1).

48. The process of claim 45, wherein pyrolysis oil is combusted to produce heat to drive step c) 1).

49. The process of claim 45, wherein the hydrocarbon gases are also converted to acetylene and residual gases in step c) 1).

50. A biofuel production process comprising:
   a) converting biomass to alcohol, methane, or mixtures thereof and residual biomass, wherein step a) comprises:
      1) fermenting biomass to produce carboxylic acids or carboxylic acid salts;
      2) thermally converting the carboxylic acids or carboxylic acid salts to ketones; and
      3) hydrogenating the ketones to produce secondary alcohols;
   b) gasifying the residual biomass to produce carbon monoxide, hydrogen, or mixtures thereof, thereby producing thermal energy;
   c) synthesizing a liquid hydrocarbon fuel from the alcohol, methane or mixture thereof using some of the thermal energy produced by gasifying the residual biomass;
   f) converting a second biomass to methane and a second residual biomass or converting landfill gas to methane;
   g) reforming the methane to produce hydrogen;
   h) using the hydrogen to drive step a) 3).

51. The process of claim 50, further comprising pyrolyzing a second biomass to produce pyrolysis oil, and combusting the pyrolysis oil to drive step a) 2).

52. The process of claim 50, wherein the biomass is converted to alcohol with enzymes.

53. A biofuel production process comprising:
   a) converting biomass to alcohol, methane, or mixtures thereof and residual biomass;
   b) gasifying the residual biomass to produce carbon monoxide, hydrogen, or mixtures thereof, thereby producing thermal energy;
   c) synthesizing a liquid hydrocarbon fuel from the alcohol, methane or mixture thereof using some of the thermal energy produced by gasifying the residual biomass, wherein step c) comprises the steps of:
      1) thermally converting the methane to acetylene and residual gases;
      2) separating the acetylene from the residual gases;
      3) hydrogenating the acetylene to form ethylene;
      4) oligomerizing the ethylene to form a hydrocarbon fuel;
   f) converting a second biomass to supplemental methane and a second residual biomass or converting landfill gas to supplemental methane;
   g) steam reforming the supplemental methane to produce hydrogen;
   h) using the hydrogen to drive step c) 3).

54. The process of claim 53, further comprising recovering supplemental methane from landfill gas, and adding the supplemental methane to the methane for thermal conversion to acetylene and residual gases in step c) 1).

55. The process of claim 54, further comprising pyrolyzing a second biomass to produce pyrolysis oil, and combusting the pyrolysis oil to produce heat to drive step c) 1).

* * * * *